(12) United States Patent
Yvin et al.

(10) Patent No.: US 6,951,934 B2
(45) Date of Patent: Oct. 4, 2005

(54) METHOD FOR PREPARING FUNCTIONALIZED β-(1,3)-GLUCAN DERIVATIVES

(75) Inventors: Jean-Claude Yvin, Saint-Malo (FR); Frank Jamois, Rennes (FR); Vincent Ferrieres, Rennes (FR); Daniel Plusquellec, Noyal Chatillon sur Seiche (FR)

(73) Assignee: Laboratoires Goemar, Saint-Malo (FR)

( * ) Notice: Subject to any disclaimer, the term of this patent is extended or adjusted under 35 U.S.C. 154(b) by 0 days.

(21) Appl. No.: 10/182,976

(22) PCT Filed: Feb. 2, 2001

(86) PCT No.: PCT/FR01/00329

§ 371 (c)(1),
(2), (4) Date: Aug. 1, 2002

(87) PCT Pub. No.: WO01/57053

PCT Pub. Date: Aug. 9, 2001

(65) Prior Publication Data

US 2003/0045706 A1 Mar. 6, 2003

(30) Foreign Application Priority Data

Feb. 4, 2000 (FR) .............................................. 00 01429

(51) Int. Cl.$^7$ ........................... C07H 1/00; C07H 15/00; C07H 17/00; C07H 17/02
(52) U.S. Cl. ................................ 536/123.12; 536/17.2; 536/18.4; 536/115; 536/119; 536/120; 536/122; 536/124; 536/126
(58) Field of Search .......................... 536/123.12, 18.4, 536/17.2, 115, 119, 120, 122, 124, 126

(56) References Cited

U.S. PATENT DOCUMENTS

| 4,719,202 A | * | 1/1988 | van Boeckel et al. | ......... 514/61 |
| 5,721,368 A | * | 2/1998 | Brands | ........................ 548/527 |
| 6,632,940 B1 | * | 10/2003 | Yvin et al. | ............. 536/123.13 |

OTHER PUBLICATIONS

Ziegler et al, "Prearranged Glycosides, Part 6: Double Asymmetric Induction During Intramolecular Glycosylation", European Journal of Organic Chemistry, vol. 1998, No. 1, pp. 163–170, 1998.*

Takeo et al. "Synthesis of the laminara–oligosacaharide beta–glycosides of dp 3–8". Carbohydrate Research, vol. 245, pp. 81–96, 1993.

Collins et al. "A new cycloglucohexasoe derivative of the chemical synthesis of cyclo {-3-beta-D-Glcp-(1-3-!5!-D-Glcp-1-}". Tetrahedron Letters, vol. 31, No. 31, pp. 45174520, (1990).

Paulson et al. "Synthese von verzweigten tetrasaccharid–und pentasaccharide–strukturen von N–glycoprotein, methyliert an 4'–OH des verzweigungsgliedes" Liebigs Ann. Chem., pp. 1303–1313, (1992).

Ziegler et al. "Intramolecular glycosylation of prearranged glycosides part 5 alpha–(1>4)–selective glucosylation of glucosides and glucosamines". Tetrahedron Letters, vol. 38, No. 21, pp. 37153718, May 26, 1997.

Fugedi et al. "Synthesis of a branched heptasaccharide having a phytoalexin–elicitor activity". Carbohydrate Research, vol. 164, pp. 297–312, (1987).

Garegg et al. "Synthesis of methyl (ethyle 2–0–acyl–3, 4–di–0–benzyl–1–thio–beta–D–glucopyranoside)uronates and evaluation of their use as reactive beta–selective glucuronic acid donore". Journal of Organic Chemistry vol. 60, pp. 2200–2204, 1995.

Xia et al. "Use of 1,2,–dichloro 4,5–dicyanoquinone (DDQ) for cleavage of the 2–naphthymethyl (NAP) group". Tetrahedron Letters, vol. 41, No. 2, pp. 169–173, 2000.

Nilsson et al. "Synthesis of a spacer–containing nonasaccharide fragment of Streptococcus pneumoniae 19F capsular polysaccharide". Journal Chem. Soc., vol. 1, pp. 1699–1704, 1998.

Nilsson et al. "Synthesis of the methyl glycosides of a tri– and a tetra–saccharide related to heparin and heparan sulphate". Carbohydrate Research, vol. 246, pp. 361–372, Aug. 17, 1993.

Gridley et al. "Regioselective Lipase–catalysed acylation of 4,6,–O–benzylidene–beta–D–pyranoside derivatives displaying a range of anomeric substituents" Synlett, pp. 1397–1399, Dec. 1997.

Verduyn et al. Synthesis of a methyl heptaglucoside: analogue of the phytoalexin elicitor from phytophtora megasperma. Tetranderon, vol. 49, No. 33, pp. 7301–7316, 1993.

Matsuo et al. "A new strategy for the synthesis of the core trisaccharide of asparagines–linked sugar chains".Tetrahedron Letters, vol. 37, No. 48, pp. 8795–8798, 1996.

Bousquet et al. "Capsular polysacchardie of Streptococcus pneumoniae type 19F: synthesis of the repeating unit". Carbohydrate Research, vol. 311, pp. 171–181, 1998.

Ziegler et al. "Synthetic studies toward pyruvate acetal containing saccharides. Synthesis of the carbohydrate part of the Mycobactrium smegmatis pentasaccharide glycolipid and fragments thereof for the preparation neoantigens" Journal Org. Chem, vol. 58, pp. 1090–1092, 1993.

* cited by examiner

Primary Examiner—James O. Wilson
Assistant Examiner—Everett White
(74) Attorney, Agent, or Firm—Merchant & Gould P.C.

(57) ABSTRACT

The present invention relates to a novel method of chemically preparing functionalized derivatives of β-(1,3)-glucans, enabling obtaining oligosaccharides which are free or which comprise specific groups such as, for example, sulphate, phosphate, methyl, in pre-defined positions. This method includes a reaction between a glycosyl donor of formula (Ia) or (Ib) and a glycosyl acceptor of formula (II), defined in the claims. Application: Preparation of biologically active compounds which can be used in the agricultural, cosmetic or pharmaceutical fields.

17 Claims, No Drawings

METHOD FOR PREPARING FUNCTIONALIZED β-(1,3)-GLUCAN DERIVATIVES

The present invention relates in general to a novel method of chemically preparing functionalised derivatives of β-(1,3)-glucans, enabling obtaining oligosaccharides which are free or which comprise specific groups in pre-defined positions.

The present invention may notably be applied for the preparation of biologically active compounds which can be used in the agricultural, cosmetic or pharmaceutical fields.

It is known that numerous oligosaccharides possess a biological activity which is generally linked to the presence of specific groups (i.e. non-hydroxyl groups), such as, for example, sulphate, phosphate, methyl groups . . . on well-defined positions.

The biological activity is also linked in certain cases to the length of the oligosaccharide.

The biologically active free oligosaccharides are usually obtained by hydrolysis or acetolysis of natural polysaccharides of plant origin and in general are in the form of complex mixtures which are extremely difficult to purify.

It has already been proposed, notably in the document FR 98 04610, of a method of chemically preparing the free disaccharide commonly called Laminaribiose, which is known for its various biological activities.

This method which enables obtaining a high overall yield of Laminaribiose, and which in general comprises the reaction between a glycosyl donor and a glycosyl acceptor, is essentially characterised by a careful choice of these compounds, as well as of the promoter used during the coupling reaction.

However, this method is specific to only Laminaribiose.

The oligosaccharides which are biologically active and which comprise specific groups are in general obtained from free oligosaccharides which inevitably lead to complex mixtures which are difficult to purify, including in the case in which the starting oligosaccharide is of perfectly defined structure. In general, the longer the oligosaccharide, the more the mixture obtained is complex and difficult to purify.

The chemical preparation of selectively functionalised derivatives of β-(1,3)-glucans enabling obtaining oligosaccharides which are free or which comprise specific groups in pre-defined positions comes notably up against the difficulty in differentiating the hydroxyl functions both with respect to each monosaccharide unit, and more particularly with respect to the positions 2, and 3, as well as with respect to the polysaccharide.

There does therefore exist a need, which is not satisfied to this day, to have at one's disposal a general method enabling the preparation of functionalised derivatives of β-(1,3)-glucans varies, which has a limited number of steps, which is compatible with a vast choice of different types of protecting groups, which is easy to implement and which enables obtaining the products sought after in a pure form.

The expression <<selectively functionalised derivatives>> used within the context of the present description thus covers compounds each position of which can be selectively converted chemically into a specific group such as, for example, a sulphate, phosphate or methyl group.

It has been discovered, and this constitutes the basis of the present invention, that it was possible to answer to this need by the use of original glycosyl donors and glycosyl acceptors which can furthermore be prepared in a single, same synthetic route from glucose.

Thus, according to a first aspect, an object of the present invention is a method for the preparation of functionalised derivatives of β-(1,3)-glucans comprising a reaction between a glycosyl donor and a glycosyl acceptor, characterised in that the glycosyl donor is selected from the group consisting of the compounds of general formulae Ia and Ib:

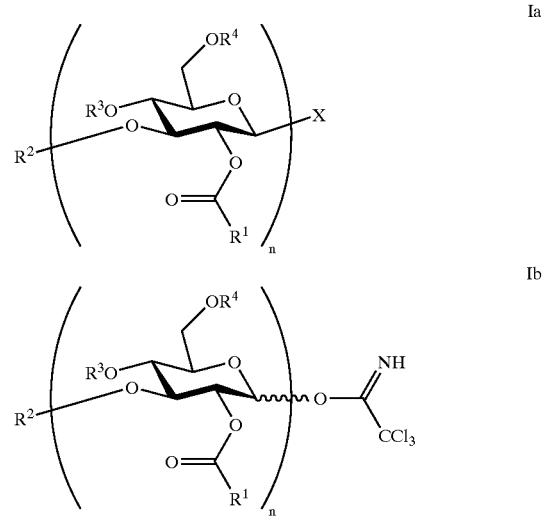

in which:

X represents a leaving group selected from:

a group of formula $S(O)_p R_a$, in which $R_a$ represents an alkyl radical having 1 to 18 carbon atoms, a 1,1-dicyclohexylmethyl radical, an aryl radical which is non-substituted or substituted with an alkyl or alkoxy group having 1 to 6 carbon atoms, a nitro or acetamide group and p is an integer equal to 0 or 1;

$R^1$ represents:

an alkyl, haloalkyl or ketoalkyl radical having 1 to 6 carbon atoms;

an aryl radical which is non-substituted or substituted with one or more groups selected from a halogen atom, an alkoxy radical having 1 to 6 carbon atoms or a nitro group;

$R^3$ and $R^4$, which are different from —CO—$R^1$ and from $R^2$, independently represent a benzyl, chlorobenzyl, methoxybenzyl, nitrobenzyl, allyl, methylnaphthyl, chloroacetyl, trialkylsilyl or triarylmethyl radical;

or together form an ethylidyl, isopropylidyl, hexafluoroisopropylidyl, cyclopentylidyl, cyclohexylidyl, cycloheptylidyl, butylidyl, 1-tert-butylethylidyl, benzylidyl, methoxybenzylidyl, or 1-phenylbenzylidyl radical.

$R^2$ represents:

a group which is different from —$COR^1$ and which is selected from a methyl, allyl, methylnaphthyl, benzyl or paramethoxybenzyl radical;

n is an integer of between 1 and 4; it being specified that in the case in which n is greater than 1, it is possible for —$COR^1$, $R^3$ and $R^4$ to be different from one glucosyl unit and another;

and in that the glycosyl acceptor is selected from the group consisting of the compounds of general formulae II:

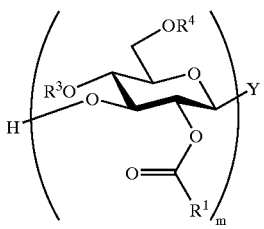

in which
Y represents a group selected from
a group of formula —O—$R_b$ in which $R_b$ represents an alkyl radical having 1 to 24 carbon atoms, an alkenyl radical having 2 to 24 carbon atoms or an arylalkylaryl or arylalkyl radical having 6 to 18 carbon atoms;
a serine or threonine residue;
a sterol residue;
a glycerolipid residue;
a group of formula —S—$R_a$ in which $R_a$ is as defined above;
$R^1$, $R^3$ and $R^4$ are as defined above, and;
m is an integer of between 1 and 8, it being specified that in the case in which m is greater than 1, it is possible for —$COR^1$, $R^3$ and $R^4$ to be different from one glucosyl unit and another.

In the description and claims:
the expression <<alkyl radical>> is understood as meaning any linear or branched hydrocarbon chain, a radical having 1 to 6 carbon atoms being for example a methyl, ethyl, propyl, isopropyl, butyl, isobutyl, tert-butyl, pentyl, isopentyl, hexyl or isohexyl radical;
the expression <<alkenyl radical>> is understood as meaning any linear or branched hydrocarbon chain comprising a double bond;
the expression <<alkoxy radical>> is understood as meaning any radical of formula —O—R in which R is an alkyl radical as defined above;
the expression <<haloalkyl radical having 1 to 6 carbon atoms" is understood as meaning any alkyl radical 1 to 7 hydrogen atoms of which have been substituted with 1 to 7 halogen atoms, such as, for example, a chloromethyl radical, a bromomethyl radical, a trifluoromethyl radical, a 2,2,2-trifluoroethyl radical, a pentafluoroethyl radical, a heptafluoropropyl radical;
the expression <<aryl radical>> is understood as meaning an aromatic ring having 5 or 6 carbon atoms or heteroatoms, such as, for example, a phenyl, pyridyl, thienyl, furanyl or pyrimidyl radical.

The method according to the invention is particularly interesting since it enables easy access to a multitude of compounds which are selectively functionalised in predetermined positions.

The specific groups which can be introduced into these predetermined positions according to the method of the invention can be of various nature and will in general be sulphate, phosphate, methyl groups, notably in positions 2, 3, 4 and 6. This method also enables fixing original residues, which are particularly interesting from a biological point of view, onto the anomeric position of the reducing unit of the oligosaccharide, notably in the case in which Y represents a serine or threonine residue, a sterol residue, or a glycerolipid residue.

According to a particular characteristic of the method according to the invention, the glycosyl donor cited above is selected from the group consisting of the compounds of general formulae (Ia) or (Ib) cited above in which:
X represents a leaving group selected from:
a group of formula $S(O)_p R_a$, in which $R_a$ represents an alkyl radical having 1 to 5 carbon atoms, a non-substituted aryl radical, preferably a phenyl radical or an aryl radical which is substituted with an alkyl group having 1 to 6 carbon atoms, preferably a toluyl radical, and p is an integer equal to 0 or 1;
$R^1$ represents:
an alkyl radical having 1 to 6 carbon atoms, preferably a methyl radical, or a levulinyl group;
a non-substituted aryl radical, preferably a phenyl radical
$R^3$ and $R^4$, which are different from —CO—$R^1$ and from $R^2$, independently represent a benzyl, chlorobenzyl, methoxybenzyl, nitrobenzyl, allyl, methylnaphthyl, chloroacetyl, trialkylsilyl or triarylmethyl radical;
or together form an ethylidyl, isopropylidyl or benzylidyl radical
$R^2$ represents:
a group which is different from —$COR^1$ and which is selected from a methyl, allyl, methylnaphthyl, benzyl or paramethoxybenzyl radical;
n is an integer equal to 1, 2 or 3; it being specified that in the case in which n is equal to 2 or 3, it is possible for —$COR^1$, $R^3$ and $R^4$ to be different from one glucosyl unit and another.

Advantageously, the glycosyl donor cited above is selected from the group consisting of the compounds of general formulae (Ia) or (Ib) cited above in which:
X represents a leaving group selected from:
a group of formula $SR_a$ in which $R_a$ represents an ethyl, propyl, butyl, phenyl or toluyl radical, preferably an ethyl or phenyl radical;
$R^1$ represents a methyl or phenyl radical
$R^3$ and $R^4$, which are different from —CO—$R^1$ and from $R^2$, independently represent a benzyl or methoxybenzyl radical
or together form a benzylidyl radical
$R^2$ represents a group which is different from —$COR^1$ and which is selected from an allyl, methylnaphthyl radical, preferably an allyl or methylnaphthyl radical;
n is an integer equal to 1 or 2; preferably equal to 1; it being specified that in the case in which n is equal to 2, it is possible for —$COR^1$, $R^3$ and $R^4$ to be different from one glucosyl unit and another.

According to another particular characteristic of the method of the invention, the glycosyl acceptor cited above is selected from the group consisting of the compounds of general formula (II) cited above in which Y represents a group selected from:
- a group of formula —O—$R_b$ in which $R_b$ represents an alkyl radical having 1 to 24 carbon atoms, an alkenyl radical having 2 to 24 carbon atoms or an arylalkylaryl or arylalkyl radical having 6 to 18 carbon atoms;
- a serine or threonine residue;
- a sterol residue;
- a glycerolipid residue;
- a group of formula —S—$R_a$ in which $R_a$ represents an alkyl radical having 1 to 5 carbon atoms, a non-substituted aryl radical, preferably a phenyl radical or an aryl radical which is substituted with an alkyl group having 1 to 6 carbon atoms $R^1$ represents:
- an alkyl radical having 1 to 6 carbon atoms, preferably a methyl radical;
- a non-substituted aryl radical, preferably a phenyl radical $R^3$ and $R^4$, which are different from —CO—$R^1$ and from $R^2$, independently represent a benzyl, chlorobenzyl, methoxybenzyl, nitrobenzyl, allyl, methylnaphthyl, chloroacetyl, trialkylsilyl or triarylmethyl radical;

or together form an ethylidyl, isopropylidyl or benzylidyl radical m is an integer of between 1 and 8, it being specified that in the case in which m is greater than 1, it is possible for —$COR^1$, $R^3$ and $R^4$ to be different from one glucosyl unit and another.

Advantageously, the glycosyl acceptor cited above is selected from the group consisting of the compounds of general formula (II) cited above in which at least one of the following conditions is fulfilled:

Y represents a group selected from:
- a group of formula —O—$R_b$ in which $R_b$ represents an alkyl radical having 1 to 24 carbon atoms, an alkenyl radical having 2 to 24 carbon atoms or a benzyl radical;

$R^1$ represents a methyl or phenyl radical;

$R^3$ and $R^4$, which are different from —CO—$R^1$, independently represent a benzyl or methoxybenzyl radical or together form a benzylidyl radical;

m is an integer of between 1 and 8, it being specified that in the case in which m is greater than 1, it is possible for —$COR^1$, $R^3$ and $R^4$ to be different from one glucosyl unit and another.

As is understood, the method according to the invention includes one or more coupling steps, according to the number of oligosaccharide units.

Generally, each step of coupling between a glycosyl donor and a glycosyl acceptor will be carried out in solution in an anhydrous organic solvent at a temperature of between −80° C. and 40° C., for a period of time of 1 minute to 8 hours in the presence of an appropriate promoter selected from:
- a source of halonium ions, which is combined or not with a Lewis acid or a salt of a strong acid in the case of the compounds of general formula (Ia) in which X represents an $S(O)_pR_a$ group as defined above and in which p is equal to 0;
- a Lewis acid combined with an amine, in the case of the compounds of general formula (Ia) in which X represents an $S(O)_pR_a$ group as defined above and in which p is equal to 1;
- a Bronsted acid or a Lewis acid, in the case of the compounds of formula (Ib).

It will be possible, for the chemical nature of the promoter, the respective amounts of the glycosyl donor, of the glycosyl acceptor and of the promoter, as well as the reaction conditions of each coupling step, to be determined easily by the person skilled in the art who will be able to refer notably to the description of the document FR 98 04610.

It will be possible for the compounds of formula (Ia), (Ib) and (II) to be prepared by various synthetic routes known in the chemistry of sugars.

Advantageously, and this constitutes an original characteristic of the invention, it will be possible for all these compounds to be prepared by a single synthetic route from glucose, and this constitutes a particularly interesting advantage from an industrial point of view.

This synthetic route, which is illustrated below by the reaction scheme (I) in the case of the monosaccharides, comprises, in the following order:
- the preparation [1] of a derivative of glucose in furanose form (X) the positions 1,2, and 5,6 of which are protected for example by acetal groups;
- the selective functionalisation [2] of the compound thus obtained in position 3 with a group corresponding to the group $R^2$ defined above, in order to form a compound (IX);
- the cleavage [3] of the protecting groups of the positions 1,2, and 5,6 of said compound (IX) in order to form a compound (VIII);
- the introduction [4], into said compound (VIII), of ester groups, preferably acetyl or benzoyl, in position 1,2 (introduction of the $COR^1$ group in position 2), 4 and 6 in order to form a compound (VII);
- the introduction [5], in anomeric position, of a thio group of formula S—$R_a$, preferably a thioethyl or thiophenyl group, in order to form a compound of formula (VI);
- the de-esterification [6] of the positions 2, 4 and 6 or [6'] of the positions 4 and 6 of compound (VI) in order to thus form compounds (IV) or (V);
- the introduction [7], [7'] and [7"], into said compounds (IV) or (V), of $R^3$ and $R^4$ groups as defined above, in order to lead to the compound (III) or to the monosaccharide (Ia) sought after;
- if need be, the esterification [8] in position 2 of said compound (III) in order to lead to the monosaccharide (Ia) sought after.

A compound is thus obtained which is selectively functionalised by the successive introduction of the groups into position 3, then 4 and 6 and then 2, or into position 3, then 2, and then 4 and 6, which enables leading to the compound sought after of formula (Ia), which enables subsequently leading, in one or two steps of glycosylation and/or of deprotection and/or of activation in the anomeric position, to a glycosyl donor or a glycosyl acceptor of formulae (Ib) and (II) in which n=1 and m=1.

REACTION SCHEME I

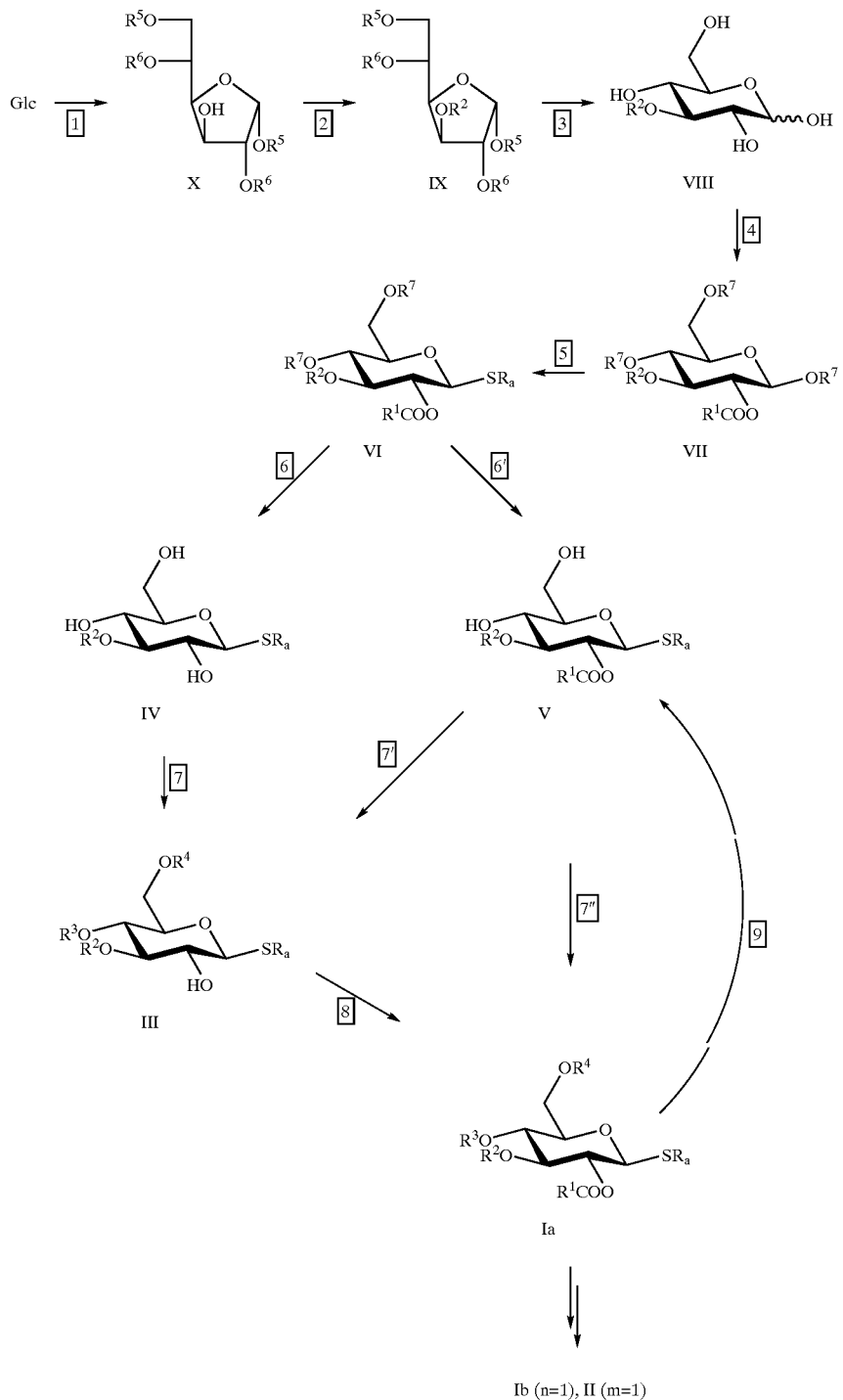

If the reaction scheme I cited above is original in some of its reaction sequences, the person skilled in the art will nevertheless have no difficulty in determining the most appropriate reaction conditions for implementing each one of the steps mentioned in this scheme.

The monosaccharides thus obtained enable easy access to other oligosaccharides (di-, tri-, etc.) of formula (Ia), (Ib) and (II).

Preferably, such an oligosaccharide will be prepared by a reaction of coupling between a monosaccharidic glycosyl donor such as obtained according to the reaction scheme (I) or a disaccharidic glycosyl donor and a monosaccharidic glycosyl acceptor such as obtained according to the reaction scheme (I), or, if need be, a polysaccharidic glycosyl acceptor such as obtained from monosaccharides by one or more prior coupling operations, and selective deprotection of the $R^2$ group.

According to a second aspect, the present application covers, as a novel product, the glycosyl donor or acceptor synthons of formula (Ia), (Ib) or (II) defined above.

The invention will now be illustrated by the following non-limiting examples, prepared by following the reaction scheme given above:

EXAMPLE 1

Preparation of Ethyl 2,4,6-tri-O-acetyl-3-O-(2-methylnaphthyl)-1-thio-β-D-gluco-pyranoside Step [2]: Preparation of 1,2:5,6-di-O-isopropylidene-3-O-(2-methylnaphthyl)-α-D-glucofuranose.

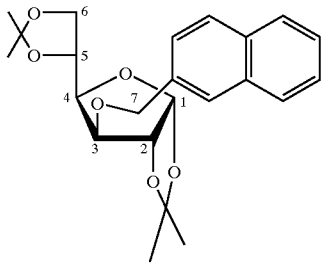

117.7 g (1 eq.) of commercial 1,2:5,6-di-O-isopropylidene-α-D-glucofuranose (M=260.28) and 100 g of 2-methylnaphthyl bromide (1 eq.) are introduced into a 2 L reactor at a temperature of 2° C. 400 mL of dimethylformamide are then added (dilution 1 in 2) and 21.7 g (1.2 eq.) of 60% sodium hydride are added to the reaction progressively over 10 minutes. The temperature is then allowed to rise slowly. After 2 hours 20 minutes, the excess of NaH is neutralised with methanol and the product is precipitated out by the addition of 2 L of iced water under vigorous agitation. 2 hours later, the supernatant is removed and the precipitate taken up into dichloromethane (1 L). After decanting, the organic phase is dried and concentrated. The crude product (M=400.5) is used directly for the following step.

TLC: Rf=0.5 [toluene/ethyl acetate (9/1; v/v)]. White solid.

$^{13}$C NMR (CDCl$_3$, 100 MHz): 135.12; 133.29; 133.11 (C quat. arom.); 128.29, 127.95, 127.78, 126.54, 126.25, 126.07, 125.71 (C arom.); 111.89, 109.011 (C quat. acetal.); 105.39 (C1); 82.73 (C2); 81.65 (C3); 81.41 (C4); 72.59 (C5); 72.49 (C7); 67.50 (C6); 26.90, 26.32, 25.54 (CH$_3$).

$^1$H NMR (CDCl$_3$, 400 MHz): 7.84–7.80 (m, 4H, H arom.); 7.49–7.45 (m, 3H, H arom.); 5.93 (d, 1H, H1, $J_{H1-H2}$=3.7 Hz); 4.85 (d, 1H, H7a, $J_{H7a-H7b}$=12.0 Hz); 4.79 (d, 1H, H7b, $J_{H7b-H7a}$=12.0 Hz); 4.63 (d, 1H, H2, $J_{H2-H1}$=3.7 Hz); 4.42 (td, 1H, H5, $J_{H5-H4}$=7.8 Hz, $J_{H5-H6a}$=$J_{H5-H6b}$=6.0 Hz); 4.16 (dd, 1H, H4, $J_{H4-H3}$=3.0 Hz, $J_{H4-H5}$=7.7 Hz); 4.14 (dd, 1H, H6a, $J_{H6a-H5}$=6.1 Hz, $J_{H6a-H6b}$=8.6 Hz); 4.08 (d, 1H, H3, $J_{H3-H4}$=3.0 Hz); 4.03 (dd, 1H, H6b, $J_{H6b-H5}$=5.8 Hz; $J_{H6b-H6a}$=8.6 Hz); 1.49, 1.43, 1.40, 1.31 (4s, 12H, CH$_3$).

Step [3]: Preparation of 3-O-(2-methylnaphthyl)-D-glucopyranose.

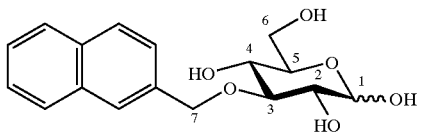

The product obtained above (M=400.5; 135 g (theoretical)) is dissolved in 270 mL of acetone and introduced into a 2 L reactor. 270 mL of water (dilution 1 in 3 in total) and then 420 g of IR 120 (H$^+$) resin are then added. The reaction medium is heated at 60° C. for 1 to 2 days (at the start, the mixture is heterogeneous and then becomes homogeneous during the reaction). Once the reaction has stopped, the resin is filtered off, rinsed with methanol and the filtrate is neutralised by the addition of a few mL of a 5% sodium bicarbonate aqueous solution. Evaporation to dryness is effected and the product is washed twice in making a suspension of the latter product in 1 L of toluene (agitation for 15 min at 40° C. and then filtration after return to ambient temperature). Finally, 116 g of 3-O-(2-methylnaphthyl)-D-glucopyranose sought after (M=320.3) are collected.

TLC: Rf=0.2 [dichloromethane/methanol (9/1; v/v)]. White solid. Yield (%)=80 for the steps [2], and [3]

$^{13}$C NMR (CD$_3$OD, 100 MHz): 137.95, 134.77, 134.44 (C quat. arom.); 128.91, 128.76, 128.62, 127.49, 127.37, 127.32, 126.94, 126.75 (C arom.); β-anomer: 98.29 (C1); 86.40 (C3); 78.01, 76.50 (C2, C5); 73.03 (C7); 71.57 (C4); 62.80 (C6); α-anomer: 94.16 (C1); 83.64 (C3); 76.25, 74.02, 73.10, 71.66 (C2, C4, C5, C7); 62.66 (C6).

$^1$H NMR (CD$_3$OD, 400 MHz): 7.78–7.31 (3 m, H arom.); 5.02 (d, 1H, H1a, $J_{H1\alpha-H2\alpha}$=3.6 Hz); 4.97 (d, 1H, H7aβ, $J_{H7a\beta-H7b\beta}$=11.3 Hz); 4.93 (d, 1H, $J_{H7b\beta-H7a\beta}$=11.3 Hz); 4.42 (d, 1H, H1b, $J_{H1\beta-H2\beta}$=7.8 Hz); 3.77 (dd, 1H, H6aβ, $J_{H6a\beta-H5\beta}$=2.4 Hz, $J_{H6a\beta-H6b\beta}$=11.9 Hz); 3.57 (dd, 1H, H6bβ, $J_{H6b\beta-H5\beta}$=5.9 Hz, $J_{H6b\beta-H6a\beta}$=11.8 Hz); 3.38 (t, 1H, H4b, $J_{H4\beta-H3\beta}$=$J_{H3\beta-H5\beta}$=9.1 Hz); 3.32 (t, 1H, $J_{H3\beta-H2\beta}$=$J_{H3\beta-H4\beta}$=8.8 Hz); 3.24–3.19 (m, 2H, H2β, H5β).

Step [5]: Preparation of 1,2,4,6-tetra-O-acetyl-3-O-(2-methylnaphthyl)-D-glucopyranose.

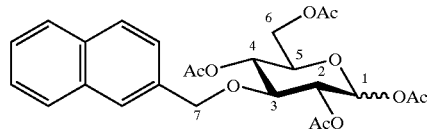

116 g (1 eq.) of 3-O-(2-methylnaphthyl)-D-glucopyranose (M=320.3), 59.4 g (2 eq.) of sodium acetate and 680 mL (20 eq.) acetic anhydride are introduced successively into a 1 L flask. The mixture is refluxed in a boiling water bath for 2 hours and then poured onto 5 L of water at ambient temperature. After a night's stirring, the precipitate obtained is filtered off and then washed with 6 L of a 5% sodium bicarbonate aqueous solution for 10 min, filtered off again and rinsed with water to neutrality and dried. The product of configuration β sought after (M=488.5) is thus obtained very mainly, in the form of a mixture of anomers β/α=86/14.

TLC: Rf=0.3 [petroleum ether/ethyl acetate (7/3; v/v)]. White solid.

$^{13}$C NMR (CDCl$_3$, 100 MHz): α-anomer: 170.88, 169.70, 169.37, 168.88 (C=O); 135.43, 133.26, 133.01 (C quat. arom.); (128.28, 127.91, 127.76, 126.37, 126.26, 126.15, 125.72, 125.54 (C arom.); 89.57 5 (C1); 77.03 (C3); 74.89 (C7); 71.62 (C2); 70.33 (C5); 69.08 (C4); 61.81 (C6); 21.01, 20.83, 20.82, 20.71 (CH$_3$).

β-anomer: 170.82, 169.38, 169.33, 169.18 (C=O); 135.01, 133.21, 133.03 (C quat. arom.); 128.33, 127.94, 127.72, 126.62, 126.35, 126.20, 125.70 (C arom.); 92.01 (C1); 79.86 (C3); 74.34 (C7); 73.02 (C5); 71.61 (C2); 69.06 (C4); 61.79 (C6); 20.94, 20.82, 20.80, 20.77 (CH$_3$).

$^1$H NMR (CDCl$_3$, 400 MHz): α-anomer: 7.83–7.81 (m, 3H, H arom.); 7.70 (s, 1H, H arom.); 7.51–7.41 (m, 2H, H arom.); 7.37–7.35 (m, 1H, H arom.); 6.32 (d, 1H, H1, $J_{H1-H2}$=3.7 Hz); 5.20 (t, 1H, H4, $J_{H4-H3}$=$J_{H4-H5}$=9.8 Hz); 5.11 (dd, 1H, H2, $J_{H2-H1}$=3.7 Hz, $J_{H2-H3}$=10.0 Hz); 4.87 (d, 1H, $J_{H7a\text{-}H7b}$=12.1 Hz); 4.78 (d, 1H, H7b, $J_{H7b\text{-}H7a}$=12.1 Hz); 4.21 (dd, 1H, H6a, $J_{H6a\text{-}H5}$=4.3 Hz, $J_{H6a\text{-}H6b}$=12.5 Hz); 4.07 (dd, 1H, H6b, $J_{H6b\text{-}H5}$=2.4 Hz, $J_{H6b\text{-}H6a}$=12.5 Hz); 4.02 (t, 1H, H3, $J_{H3\text{-}H2}$=$J_{H3\text{-}H4}$=9.7 Hz); 4.01 (ddd, 1H, H5, $J_{H5\text{-}H4}$=10.2 Hz, $J_{H5\text{-}H6a}$=4.2 Hz, $J_{H5\text{-}H6b}$=2.4 Hz); 2.16, 2.09, 1.98, 1.92 (4s, 12H, CH$_3$).

β-anomer: 7.83–7.80 (m, 3H, H arom.); 7.69 (s, 1H, H arom.); 7.51–7.46 (m, 2H, H arom.); 7.36–7.33 (m, 1H, H arom.); 5.66 (d, 1H, H1, $J_{H1\text{-}H2}$=8.2 Hz); 5.21 (dd, 1H, H2, $J_{H2\text{-}H1}$=8.2 Hz, $J_{H2\text{-}H3}$=9.5 Hz); 5.20 (t, 1H, H4, $J_{H4\text{-}H3}$=$J_{H4\text{-}H5}$=9.5 Hz); 4.78 (s, 2H, H7a, H7b); 4.23 (dd, 1H, H6a, $J_{H6a\text{-}H5}$=4.8 Hz, $J_{H6a\text{-}H6b}$=12.5 Hz); 4.09 (dd, 1H, H6b, $J_{H6b\text{-}H5}$=2.4 Hz, $J_{H6b\text{-}H6a}$=12.2 Hz); 3.81 (t, 1H, H3, $J_{H3\text{-}H2}$=$J_{H3\text{-}H4}$=9.3 Hz); 3.74 (ddd, 1H, H5, $J_{H5\text{-}H4}$=10.0 Hz, $J_{H5\text{-}H6a}$=4.8 Hz, $J_{H5\text{-}H6b}$=2.3 Hz); 2.10, 2.08, 1.94, 1.93 (4s, 12H, CH$_3$).

Step 5: Preparation of Ethyl 2,4,6-tri-O-acetyl-3-O-(2-methylnaphthyl)-1-thio-β-D-glucopyranoside.

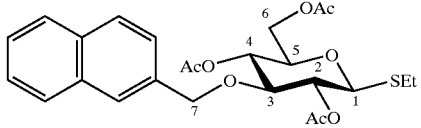

177 g (1 eq.) (theoretical) of 1,2,4,6-tetra-O-acetyl-3-O-(2-methylnaphthyl)-D-glucopyranose obtained above (M=488.5) and then 885 mL (dilution 1 in 5) of dichloromethane are dissolved in a 2 L reactor. The medium is cooled to 0° C. and then 20.5 mL (1.1 eq.) of ethanethiol are added. 50.1 mL (1.1 eq.) of boron trifluoride etherate (addition over 20 min) are added dropwise slowly. After 2 hours at 0° C., washing is effected twice with 1 L of a 5% sodium bicarbonate aqueous solution (the red-coloured solution becomes pale yellow), once with 500 mL of water and then the organic phase is dried (MgSO$_4$) and evaporated. The crude product isolated (M=490.6) is used as such for the next step.

TLC: Rf=0.4 [petroleum ether/ethyl acetate (7/3; v/v)]. White solid.

$^{13}$C NMR (CDCl$_3$, 100 MHz): 170.89, 149.46, 169.43 (C=O); 135.27, 133.25, 133.02 (3 C quat. arom.); 128.29, 127.95, 127.74, 126.52, 126.32, 126.14, 125.73 (7 C quat. arom.); 83.75 (C1); 81.51 (C3); 76.25, 74.32, 71.31, 69.70 (C2, C4, C5, C7); 62.54 (C6); 24.03 (CH$_2$[SEt]); 21.13, 20.87 (CH$_3$[Ac]); 14.85 (CH$_3$[SEt]).

$^1$H NMR (CDCl$_3$, 400 MHz): 7.83–7.80 (m, 3H, H arom.); 7.68 (s, 1H, H arom.); 7.50–7.46 (m, 2H, H arom.); 7.35–7.33 (m, 1H, H arom.); 5.14 (t, 1H, H2 or H4, 3=9.9 Hz); 5.12 (t, 1H, H2 or H4, J=9.7 Hz); 4.80 (d, 1H, H7a, $J_{H7a\text{-}H7b}$=12.0 Hz); 4.75 (d, 1H, H7b, $J_{H7b\text{-}H7a}$=12.1 Hz); 4.40 (d, 1H, H1, $J_{H1\text{-}H2}$=10.0 Hz); 4.19 (dd, 1H, H6a, $J_{H6a\text{-}H5}$=5.1 Hz, $J_{H6a\text{-}H6b}$=12.3 Hz); 4.11 (dd, 1H, H6b, $J_{H6b\text{-}H5}$=2.4 Hz, $J_{H6b\text{-}H6a}$=12.2 Hz); 3.76 (t, 1H, H3, $J_{H3\text{-}H2}$=$J_{H3\text{-}H4}$=9.2 Hz); 3.60 (ddd, 1H, H5, $J_{H5\text{-}H4}$=10.0 Hz, $J_{H5\text{-}H6a}$=5.1 Hz, $J_{H5\text{-}H6b}$=2.5 Hz); 2.77–2.63 (m, 2H, CH$_2$[SEt]); 2.07, 1.98, 1.92 (3s, 9H, CH$_3$); 1.24 (t, 3H, CH$_3$[SEt], J=7.4 Hz).

EXAMPLE 2

Preparation of a Glycosyl Donor of General Formula (Ia) According to the Invention, Product of Example 1 and then of Steps 7 and 8

Step 7: Preparation of Ethyl 2-O-acetyl-3-O-2-methylnaphthyl)-1-thio-β-D-glucopyranoside.

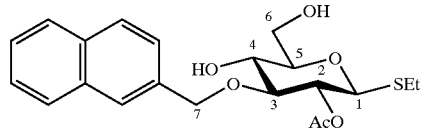

178 g (1 eq.) (theoretical) of ethyl 2,4,6-tri-O-acetyl-3-O-2-methylnaphthyl)-1-thio-β-D-glucopyranoside (M=490.6) are dissolved in the hot (40° C.) in 180 mL of toluene and poured onto 900 mL (dilution 1 in 5) of methanol. The solution is limpid. The return to R.T. is accompanied by a progressive precipitation of the product until a suspension is obtained. 0.05 eq. of sodium in the form of a solution of sodium methoxide obtained by dissolving 417 mg of sodium in 50 mL of methanol, are then added slowly. After half an hour, the solution becomes perfectly limpid again. After 3 hours 30 minutes of reaction, the medium is neutralised with IR 120 (H$^+$) resin, filtered and concentrated. The oily residue obtained is poured onto 1.5 L of heptane: the product precipitates. After filtration, the residue is taken up with 1 L of dichloromethane and the reaction coproducts are removed by 2 washings in the hot (35–40° C.) with 1 L of water. The organic phase is recovered, dried and evaporated in order to lead to 95 g of ethyl 2-O-acetyl-3-O-2-methylnaphthyl)-1-thio-β-D-glucopyranoside sought after (M=406.5).

TLC: Rf=0.5 [dichloromethane/methanol (9/1; v/v)]. White solid. Yield (%)=65 for the steps 4, 5 and 7.

$^{13}$C NMR (CDCl$_3$, 100 MHz): 169.81 (C=O); 135.48, 133.27, 133.07 (3 C quat. arom.); 128.54, 127.99, 127.78, 126.70, 126.37, 126.18, 125.69 (C arom.); 83.86 (C3); 83.77 (C1); 79.52 (C5); 74.85 (C7); 71.63 (C2); 70.46 (C4); 62.46 (C6); 24.17 (CH$_2$[SEt]); 21.17 (CH$_3$[Ac]); 14.90 (CH$_3$[SEt]).

$^1$H NMR (CDCl$_3$, 400 MHz): 7.85–7.81 (m, 3H, H arom.); 7.74 (s, 1H, H arom.); 7.50–7.45 (m, 3H, H arom.); 5.01 (dd, 1H, H2, $J_{H2\text{-}H1}$=9.9 Hz, $J_{H2\text{-}H3}$=9.2 Hz); 4.97 (d, 1H, H7a, $J_{H7a\text{-}H7b}$=11.9 Hz); 4.85 (d, 1H, H7b, $J_{H7b\text{-}H7a}$=11.8 Hz); 4.40 (d, 1H, H1, $J_{H1\text{-}H2}$=10.0 Hz); 3.88 (dd, 1H, H6a, $J_{H6a\text{-}H5}$=3.2 Hz, $J_{H6a\text{-}H6b}$=12.0 Hz); 3.78 (dd, 1H, H6b, $J_{H6b\text{-}H5}$=4.7 Hz, $J_{H6b\text{-}H6a}$=12.0 Hz); 3.72 (t, 1H, H4, $J_{H4\text{-}H3}$=$J_{H4\text{-}H5}$=9.3 Hz); 3.59 (t, 1H, H3, $J_{H3\text{-}H2}$=$J_{H3\text{-}H4}$=9.1 Hz); 3.37 (ddd, 1H, H5, $J_{H5\text{-}H4}$=9.5 Hz, $J_{H5\text{-}H6a}$=3.4 Hz, $J_{H5\text{-}H6b}$=4.6 Hz); 2.99 (sl, 1H, OH); 2.68 (qd, 2H, CH$_2$[SEt], J=); 2.41 (sl, 1H, OH); 2.00 (s, 3H, CH$_3$[Ac]); 1.24 (t, 3H, CH$_3$[SEt], J=7.4 Hz).

Step [8]: Preparation of Ethyl 2-O-acetyl-4,6-O-benzylidene-3-O-2-methylnaphthyl)-1-thio-β-D-glucopyranoside.

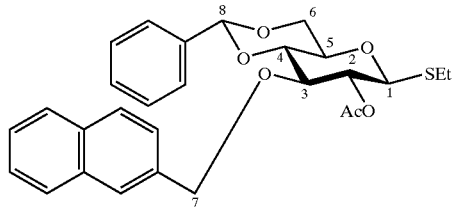

56 g (1 eq.) of ethyl 2-O-acetyl-3-O-2-methylnaphthyl)-1-thio-β-D-glucopyranoside (M=406.5) are dissolved in 300 mL (dilution 1 in 5) of acetonitrile in a 2 L reactor, and then 31.0 mL (1.5 eq.) of benzaldehyde dimethylacetal and 6.4 g (0.2 eq.) of anhydrous camphosulphonic acid (the medium turns pink) are added thereto. The mixture is heated at 55° C. for 2 hours and then cooled to R.T. and neutralised with 3.8 mL of triethylamine (discolouration: the medium becomes pale yellow). After concentration, the residue is dissolved in the minimum of dichloromethane and is poured onto 1 L of methanol: the product precipitates. After one night in the freezer, the product is filtered off, rinsed with iced methanol and then dried. 53 g of ethyl 2-o-acetyl-4,6-O-benzylidene-3-O(2-methylnaphthyl)-1-thio-β-D-glucopyranoside expected (M=494.6) are thus isolated.

TLC: Rf=0.6 [toluene/ethyl acetate (17/3; v/v)]. White solid. Yield (%)=78.

$^{13}$C NMR (CDCl$_3$, 100 MHz): 169.59 (C=O); 137.20, 135.61, 133.24, 133.03 (4 C quat. arom.); 129.15, 128.39, 128.13, 127.97, 127.72, 126.79, 126.17, 126.10, 126.02, 125.99 (C arom.); 101.36 (C8); 84.25 (C1); 81.64, 79.48 (C3, C4); 74.37 (C7); 71.28 (C2); 70.70 (C5); 68.67 (C6); 23.98 (CH$_2$[SEt]); 21.04 (CH$_3$[Ac]); 14.86 (CH$_3$[SEt]).

$^1$H NMR (CDCl$_3$, 400 MHz): 7.83–7.73 (m, 4H, H arom.); 7.53–7.45 (m, 4H, H arom.); 7.42–7.39 (m, 4H, H arom.); 5.61 (s, 1H, H8); 5.12–5.07 (m, 1H, H2); 5.03 (d, 1H, H7a, $J_{H7a-H7b}$=12.2 Hz); 4.87 (d, 1H, H7b, H$_{H7b-H7a}$=12.3 Hz); 4.45 (d, 1H, H1, $J_{H1-H2}$=10.0 Hz); 4.39 (dd, 1H, H6a, $J_{H6a-H5}$=5.0 Hz, $J_{H6a-H6b}$=10.5 Hz); 3.83–3.78 (m, 3H, H3, H4, H6b); 3.50 (ddd, 1H, H5, $J_{H5-H4}$=9.5 Hz, $J_{H5-H6a}$=4.8 Hz, $J_{H5-H6b}$=9.4 Hz); 2.77–2.64 (m, 2H, CH$_2$[SEt]); 2.00 (s, 3H, CH$_3$[Ac]); 1.25 (t, 3H, CH$_3$[SEt], J=7.4 Hz).

EXAMPLE 3

Preparation of a Glycosyl Donor of General Formula (Ia) According to the Invention Step [7'"]: Preparation of Ethyl 4,6-di-O-benzyl-3-O-2-methylnaphthyl)-1-thio-β-D-glucopyranoside.

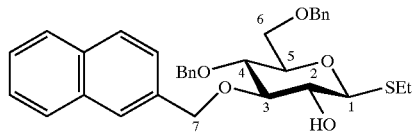

20 g (1 eq.) of ethyl 2-O-acetyl-3-O-(2-methylnaphthyl)-1-thio-□-D-gluco-pyranoside prepared in step [7] of Example 2 (M=406.5) are dissolved in 200 mL (dilution 1 in 20) of dimethylformamide at 0° C. and 13 mL (2.2 eq.) of benzyl bromide are added thereto. 4.4 g (2.2 eq.) of 60% sodium hydride are then added very progressively at 0° C. After 2 hours of reaction at ambient temperature, the excess of NaH is destroyed by the addition of methanol and the medium is diluted with 250 mL of ethyl ether and then washed twice with 30 mL of water, dried and concentrated. Purification over silica gel [flash; eluent: petroleum ether/ethyl acetate (9/1; v/v)] enables collecting 21.4 g of ethyl 4,6-di-O-benzyl-3-O-2-methylnaphthyl)-1-thio-β-D-glucopyranoside sought after (M=544.7).

TLC: Rf=0.3 [petroleum ether/ethyl acetate (8/2; v/v)]. Whited solid. Yield (%)=80.

$^{13}$C NMR (CDCl$_3$, 100 MHz): 138.19, 138.10, 136.08, 133.36, 133.03 (5 C quat. arom.); 128.43, 128.38, 128.29, 127.98, 127.79, 127.72, 127.64, 126.69, 126.09, 126.04, 125.90 (C arom.); 86.16 (C1); 85.98 (C3); 79.46 (C5); 77.46 (C4); 75.28 (CH$_2$[Bn]); 75.12 (C7); 73.42 (CH$_2$[Bn]); 73.34 (C2); 69.05 (C6); 24.32 (CH$_2$); 15.46 (CH$_3$).

$^1$H NMR (CDCl$_3$, 400 MHz): 7.73–7.67 (m, 4H, H arom.); 7.46–7.35 (m, 3H, H arom.); 7.26–7.17 (m, 8H, H arom.); 7.09–7.07 (m, 2H, H arom.); 5.02 (d, 1H, CH$_2$[Bn], J=11.5 Hz); 4.92 (d, 1H, CH$_2$[Bn], J=11.6 Hz); 4.78 (d, 1H, H7a, $J_{H7a-H7b}$=10.9 Hz); 4.52 (d, 1H, CH$_2$[Bn], J=11.9 Hz); 4.49 (d, 1H, H7b, $J_{H7b-H7a}$=9.7 Hz); 4.45 (d, 1H, CH$_2$[Bn], J=12.2 Hz); 4.23 (d, 1H, H1, $J_{H1-H2}$=10.2 Hz); 3.67 (dd, 1H, H6a, $J_{H6a-H5}$=1.9 Hz, $J_{H6a-H6b}$=10.9 Hz); 3.62 (dd, 1H, H6b, $J_{H6b-H5}$=4.5 Hz, $J_{H6b-H6a}$=10.9 Hz); 3.59–3.47 (m, 3H, H2, H3, H4); 3.43 (m, 1H, H5); 2.72–2.58 (m, 2H, CH$_2$); 2.40 (s, 1H, OH); 1.23 (t, 3H, CH$_3$, J=7.4 Hz).

Step [6']: Preparation of Ethyl 4,6-di-O-benzyl-3-O-methylnaphthyl-1-thio-β-D-glucopyranoside.

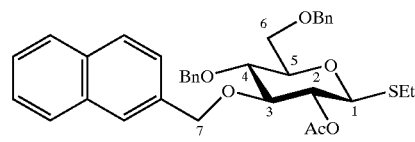

21 g (1 eq.) of ethyl 4,6-di-O-benzyl-3-O-2-methylnaphthyl)-1-thio-β-D-glucopyranoside sought after (M=544.7) are dissolved in 100 mL of pyridine and 10.9 mL (3 eq.) of acetic anhydride are added thereto. Once the reaction has stopped, the medium is diluted with water: the product sought after precipitates. After filtration, the latter is taken up into dichloromethane, washed with a 10% solution of hydrochloric acid, a 5% sodium bicarbonate solution, and then with water. 21 g of ethyl 4,6-di-O-benzyl-3-O-methylnaphthyl-1-thio-β-D-glucopyranoside (M=586.8) are thus collected.

TLC: Rf=0.4 [petroleum ether/ethyl acetate (8/2; v/v)]. White solid. Yield (%)=95.

$^{13}$C NMR (CDCl$_3$, 100 MHz): 169.76 (C=O); 138.20, 137.95, 135.71, 133.31, 133.02 (5 C quat. arom.); 128.50, 128.43, 128.25, 128.09, 127.99, 127.92, 127.77, 127.73, 127.67, 126.53, 126.20, 126.01, 125.89 (C arom.); 84.40 (C3 or C4); 83.46 (C1); 79.55 (C5); 78.00 (C3 or C4); 75.31 (CH$_2$[Bn]); 75.19 (C7); 73.52 (CH$_2$[Bn]); 71.82 (C2); 68.91 (C6); 23.83 (CH$_2$[SEt]); 21.07 (CH$_3$[Ac]); 14.97 (CH$_3$[SEt]).

$^1$H NMR (CDCl$_3$, 400 MHz): 7.75–7.69 (m, 3H, H arom.); 7.63 (s, 1H, H arom.); 7.41–7.38 (m, 2H, H arom.); 7.32–7.30 (s, 1H, H arom.); 7.26–7.19 (m, 10H, H arom.); 7.11–7.08 (m, 2H, H arom.); 5.02–4.97 (m, 1H, H2); 4.88 (d, 1H, CH$_2$[Bn], J=11.7 Hz); 4.77 (d, 1H, CH$_2$[Bn], J=11.7 Hz); 4.73 (d, 1H, H7a, $J_{H7a-H7b}$=10.8 Hz); 4.54 (d, 1H, CH$_2$[Bn], 3=12.0 Hz); 4.51 (d, 1H, H7b, $J_{H7b-H7a}$=9.4 Hz); 4.48 (d, 1H, CH$_2$[Bn], J=12.2 Hz); 4.28 (d, 1H, H1, $J_{H1-H2}$=10.0 Hz); 3.69 (dd, 1H, H6a, $J_{H6a-H5}$=2.0 Hz, $J_{H6a-H6b}$=10.9 Hz); 3.68–3.63 (m, 3H, H3, H4, H6b); 3.44 (ddd, 1H, H5, $J_{H5-H4}$=9.2 Hz, $J_{H5-H6a}$=2.1 Hz, $J_{H5-H6b}$=4.1 Hz);

2.71–2.56 (m, 2H, CH$_2$[SEt]); 1.84 (s, 3H, CH$_3$[Ac]); 1.18 (t, 3H, CH$_3$[SEt], J=7.4 Hz).

EXAMPLE 4

Preparation of a Glycosyl Donor of General Formula (Ia) According to the Invention, Product of Example 1 and and then of Steps [6], [7] and[6']

Step [6]: Preparation of Ethyl 3-O-2-methylnaphthyl)-1-thio-β-D-glucopyranoside.

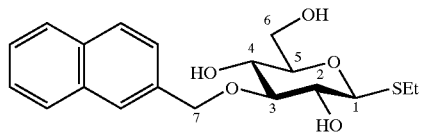

2 L of methanol containing 7.03 g (1.5 eq.)(theoretical) are added progressively 100 g of ethyl 2,4,6-tri-O-acetyl-3-O-2-methylnaphthyl)-1-thio-β-D-glucopyr-anoside prepared in Example 1 (M=490.6) dissolved in 100 mL of toluene. After 4 hours of reaction at ambient temperature, the medium is neutralised with IR 120 (H$^+$) resin, filtered and concentrated. The oily residue obtained is poured onto 1 L of heptane: the product precipitates. After filtration, the residue is taken up with 0.6 L of dichloromethane and the reaction coproducts are removed by 2 washings in the hot (35–40° C.) with 0.6 L of water. The organic phase is recovered, dried and evaporated in order to lead to 49.8 g of ethyl 3-O-2-methylnaphthyl)-1-thio-β-D-glucopyranoside (M=364.5).

TLC: Rf=0.5 [dichloromethane/methanol (9/1; v/v)]. White solid. Yield (%)=67 for the steps [4], [5] and [6].

$^{13}$C NMR (CDCl$_3$, 100 MHz): 135.83, 133.36, 133.12 (3 C quat. arom.); 128.62, 128.01, 127.83, 126.99, 126.34, 126.15, 125.91 (C arom.); 86.70 (C1); 85.00 (C3); 79.48 (C5); 74.91 (C7); 73.23 (C2); 70.13 (C4); 62.74 (C6); 24.74 (CH$_2$[SEt]); 15.49 (CH$_3$[SEt]).

$^1$H NMR (CDCl$_3$, 400 MHz): 7.86–7.82 (m, 4H, H arom.); 7.51–7.47 (m, 3H, H arom.); 5.17 (d, 1H, H7a, J$_{H7a-H7b}$=11.8 Hz); 4.94 (d, 1H, H7b, J$_{H7b-H7a}$=11.8 Hz); 4.36 (d, 1H, H1, J$_{H1-H2}$=9.6 Hz); 3.87 (dd, 1H, H6a, J$_{H6a-H5}$=3.3 Hz, J$_{H6a-H6b}$=12.0 Hz); 3.75 (dd, 1H, H6b, J$_{H6b-H5}$=4.9 Hz, J$_{H6b-H6a}$=12.0 Hz); 3.62 (t, 1H, H4, J$_{H4-H3}$=J$_{H4-H5}$=9.2 Hz); 3.53 (t, 1H, H2, J$_{H2-H1}$=J$_{H2-H3}$=9.0 Hz); 3.46 (t, 1H, H3, J$_{H3-H2}$=J$_{H3-H4}$=8.6 Hz); 3.37 (ddd, 1H, H5, J$_{H5-H4}$=9.2 Hz, J$_{H5-H6a}$=3.5 Hz, J$_{H5-H6b}$=4.8 Hz); 2.73 (qd, 2H, CH$_2$[SEt]); 2.68 (sl, 1H, OH); 2.56 (s, 1H, OH); 2.22 (sl, 1H, OH); 1.33 (t, 3H, CH$_3$[SEt], J=7.4 Hz).

Step [7]: Preparation of Ethyl 4,6-O-benzylidene-3-O-2-methylnaphthyl)-1-thio-β-D-glucopyranoside.

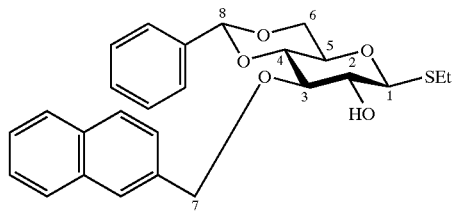

50 g (1 eq.) of ethyl 3-O-2-methylnaphthyl)-1-thio-β-D-glucopyranoside (M=364.5) are dissolved in 300 mL (dilution 1 in 5) of acetonitrile in a 2 L reactor. 31.0 mL (1.5 eq.) of benzaldehyde dimethylacetal and 6.4 g (0.2 eq.) of anhydrous camphorsulphonic acid (the medium turns pink) are added thereto. The mixture is heated at 55° C. for 2 hours and then cooled to R.T. and neutralised with 3.8 mL of triethylamine (discolouration: the medium becomes pale yellow). After concentration, the residue is dissolved in the minimum of dichloromethane and poured onto 1 L of methanol: the product precipitates. After one night in the freezer, the product is filtered off, rinsed with iced methanol and then dried. 48.5 g of ethyl 4,6-O-benzylidene-3-O-2-methylnaphthyl)-1-thio-β-D-glucopyranoside expected (M=452.6) are thus isolated.

TLC: Rf=0.4 [toluene/ethyl acetate (17/3; v/v)]. White solid. Yield (%)=78.

$^{13}$C NMR (CDCl$_3$, 100 MHz): 137.30, 135.80, 133.33, 133.10 (4 C quat. arom.); 129.10, 128.35, 128.30, 128.01, 127.74, 126.90, 126.14, 126.11, 126.05, 125.95 (C arom.); 101.41 (C8); 86.71 (C1); 81.47, 81.25 (C3, C4); 74.74 (C7); 73.19 (C2); 70.83 (C5); 68.72 (C6); 24.64 (CH$_2$); 15.31 (CH$_3$).

$^1$H NMR (CDCl$_3$, 400 MHz): 7.82–7.74 (m, 4H, H arom.); 7.53–7.39 (m, 8H, H arom.); 5.60 (s, 1H, H8); 5.14 (d, 1H, H7a, J$_{H7a-H7b}$=12.0 Hz); 5.01 (d, 1H, H7b, J$_{H7b-H7a}$=12.0 Hz); 4.46 (d, 1H, H1, J$_{H1-H2}$=9.7 Hz); 4.37 (dd, 1H, H6a, J$_{H6a-H5}$=5.0 Hz, J$_{H6a-H6b}$=10.4 Hz); 3.79 (t, 1H, H6b, J$_{H6b-H5}$=J$_{H6b-H6a}$=10.3 Hz); 3.76–3.71 (m, 2H, H3, H4); 3.63 (dd, 1H, H2, J$_{H2-H1}$=9.0 Hz, J$_{H2-H3}$=8.4 Hz); 3.50 (ddd, 1H, H5, J$_{H5-H4}$=J$_{H5-H6b}$=9.5 Hz, J$_{H5-H6a}$=5.1 Hz); 2.82–2.69 (m, 2H, CH$_2$); 2.61 (s, 1H, OH); 1.32 (t, 3H, CH$_3$, J=7.4 Hz).

Step [6']: Preparation of Ethyl 2-O-benzoyl-4,6-O-benzylidene-3-O-2-methylnaphthyl)-1-thio-β-D-glucopyranoside.

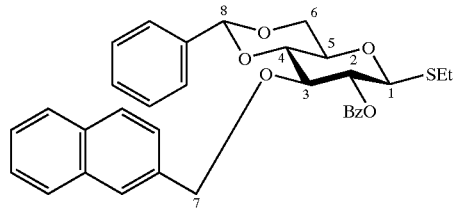

37 ml (3 eq.) of benzoyl chloride are added slowly in one batch to 48.5 g of ethyl 4,6-O-benzylidene-3-O-2-methylnaphthyl)-1-thio-β-D-glucopyranoside (1 eq.) (M=452.6) in 300 mL of pyridine (dilution 1 in 6) and the reaction is left one night at RT. The solution is then poured onto 1 l of methanol under vigorous agitation. The product slowly precipitates and then is filtered off and rinsed with iced methanol. 50 g of ethyl 2-O-benzoyl-4,6-O-benzylidene-3-O-2-methylnaphthyl)-1-thio-β-D-glucopyranoside sought after (M=556.7) are thus collected.

TLC: Rf=0.6 [toluene/ethyl acetate (9/1; v/v)]. White solid. Yield (%)=84.

$^{13}$C NMR (CDCl$_3$, 100 MHz): 165.25 (C=O); 137.27, 135.28, 133.25, 133.09, 132.95 (5 C quat. arom.); 129.95, 129.18, 128.42, 128.11, 127.92, 127.67, 127.06, 126.25, 126.14, 125.95, 125.83 (C arom.); 101.42 (C8); 84.38 (C1); 81.81 (C4), 79.00 (C3); 74.29 (C7); 71.86 (C2); 70.76 (C5); 68.73 (C6); 24.12 (CH$_2$[SEt]); 14.88 (CH$_3$[SEt]).

$^1$H NMR (CDCl$_3$, 400 MHz): 7.95–7.92 (m, 2H, H arom.); 7.69–7.36 (3m, 12H, H arom.); 7.22 (dd, 1H, H arom.); 5.64 (s, 1H, H8); 5.36 (dd, 1H, H2, J$_{H2-H1}$=10.0 Hz, J$_{H2-H3}$=8.5 Hz); 4.98 (d, 1H, H7a, J$_{H7a-H7b}$=12.2 Hz); 4.86 (d, 1H, H7b, J$_{H7b-H7a}$=12.2 Hz); 4.59 (d, 1H, H1, J$_{H1-H2}$=10.0 Hz); 4.41 (dd, 1H, H6a, J$_{H6a-H5}$=5.0 Hz, J$_{H6a-H6b}$=10.5 Hz); 3.93 (t, 1H, H3, J$_{H3-H2}$=J$_{H3-H4}$=9.2 Hz); 3.88 (dd, 1H, H4, $J_{H4-H3}$=8.8 Hz, $J_{H4-H5}$=9.2 Hz); 3.84 (t, 1H, H6b, $J_{H6b-H5}$=$J_{H6b-H6a}$=10.3 Hz); 3.56 (ddd, 1H, H5, $J_{H5-H4}$=9.1 Hz, $J_{H5-H6a}$=5.0 Hz, $J_{H5-H6b}$=9.9 Hz); 2.77–2.64 (m, 2H, $CH_2$[SEt]); 1.21 (t, 3H, $CH_3$[SEt], J=7.4 Hz).

EXAMPLE 5

Synthesis of a Glycosyl Acceptor Synthon of General Formula (II) According to the Invention Step 5A: Preparation of Benzyl 2-O-benzoyl-4,6-O-benzylidene-3-O-(2-methylnaphthyl)-β-D-glucopyranoside Precursor.

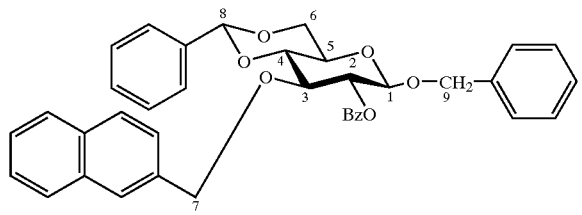

31.2 g (1 eq) of ethyl 2-O-benzoyl-4,6-O-benzylidene-3-O-2-methylnaphthyl)-1-thio-β-D-glucopyranoside (M=556.7), 13.9 g (1.1 eq.) of N-iodosuccinimide, 10 g of 4 Å molecular seives, 200 mL (dilution 1 in 5) of anhydrous dichloromethane and finally 6.96 mL (1.2 eq.) of benzyl alcohol are introduced successively into a flask at 0° C. 1.27 mL (0.1 eq.) of triethylsilyl triflate are then added. After 1 hour of reaction at 0° C., the medium is neutralised with a few drops of triethylamine, filtered off on sintered glass and concentrated. Purification over silica gel [flash; eluent: toluene/ethyl acetate (97/3; v/v)] enables collecting 30 g of benzyl 2-O-benzoyl-4,6-O-benzylidene-3-O-(2-methylnaphthyl)-β-D-glucopyranoside expected (M=602.7).

TLC: Rf=0.6 [toluene/ethyl acetate (9/1; v/v)]. White solid. Yield (%)=89.

$^{13}$C NMR (CDCl$_3$, 100 MHz): 165.14 (C=O); 137.28, 136.75, 135.32, 133.13, 133.04, 132.89 (6 C quat. arom.); 129.93, 129.77, 129.13, 128.37, 128.32, 128.29, 128.05, 127.87, 127.77, 127.67, 127.61, 126.97, 126.20, 126.13, 125.89, 125.76 (C arom.); 101.38 (C8); 99.96 (C1); 81.78 (C4); 77.57 (C3); 73.96 (C7); 73.31 (C2); 70.46 (C9); 68.76 (C6); 66.28 (C5).

$^1$H NMR (CDCl$_3$, 400 MHz): 7.89–7.86 (m, 2H, H arom.); 7.67–7.07 (m, 17H, H arom.); 5.62 (s, 1H, H8); 5.40 (t, 1H, H2, $J_{H2-H1}$=$J_{H2-H3}$=8.3 Hz); 4.95 (d, 1H, H7a, $J_{H7a-H7b}$=12.4 Hz); 4.84 (d, 2H, H7b, H9a, $J_{H7b-H7a}$=$J_{H9a-H9b}$=12.6 Hz); 4.58 (d, 1H, H9b, $J_{H9b-H9a}$=13.6 Hz); 4.58 (d, 1H, H1, $J_{H1-H2}$=7.8 Hz); 4.40 (dd, 1H, H6a, $J_{H6a-H5}$=5.0 Hz, $J_{H6a-H6b}$=10.5 Hz); 3.90 (t, 1H, H4, $J_{H4-H3}$=$J_{H4-H5}$=9.1 Hz); 3.86 (t, 1H, H6b, $J_{H6b-H5}$=$J_{H6b-H6a}$=10.2 Hz); 3.84 (dd, 1H, H3, $J_{H3-H2}$=8.5 Hz, $J_{H3-H4}$=9.1 Hz); 3.45 (ddd, 1H, H5, $J_{H5-H4}$=9.2 Hz, $J_{H5-H6a}$=5.0 Hz, $J_{H5-H6b}$=9.8 Hz).

Step 5B: Preparation of Acceptor Synthon Benzyl 2-O-benzoyl-4,6-O-benzylidene-β-D-glucopyranoside (OH in Position 3).

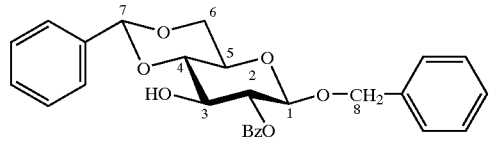

42.0 g (1 eq.) of benzyl 2-O-benzoyl-4,6-benzylidene-3-O-(2-methylnaphthyl)-β-D-glucopyranoside (M=602.7) and 47.5 g (3 eq.) of 2,3-dichloro-5,6-dicyano-1,4-benzoquinone (DDQ) are introduced into 850 mL of a dichloromethane/methanol (4/1; v/v) mixture at ambient temperature. After 5 hours 30 minutes, the medium is diluted with 1 L of dichloromethane and washed twice with a 5% sodium bicarbonate aqueous solution. After drying and evaporation of the organic phase, the residue is purified over silica gel [flash; eluent: toluene/ethyl acetate (9/1; v/v)]. 27.4 g of benzyl 2-O-benzoyl-4,6-O-benzylidene-□-D-glucopyranoside expected (M=462.5) are thus obtained.

TLC: Rf=0.3 [toluene/ethyl acetate (9/1; v/v)]. White solid. Yield (%)=85.

$^{13}$C NMR (CDCl$_3$, 100 MHz): 165.97 (C=O); 136.97, 136.73, 133.37 (3 C quat. arom.); 130.05, 129.59, 129.37, 128.41, 127.93, 127.84, 126.37 (C arom.); 101.96 (C7); 99.75 (C1); 80.94 (C4); 74.82 (C2); 72.41 (C3); 70.63(C8); 68.66 (C6); 66.26 (C5).

$^1$H NMR (CDCl$_3$, 400 MHz): 8.03–8.00 (m, 2H, H arom.); 7.62–7.58 (m, 1H, H arom.); 7.52–7.43 (m, 4H, H arom.); 7.41–7.36 (m, 3H, H arom.); 7.23–7.19 (m, 5H, H arom.); 5.57 (s, 1H, H7); 5.26 (dd, 1H, H2, $J_{H2-H1}$=7.9 Hz, $J_{H2-H3}$=9.1 Hz); 4.89 (dd, 1H, H8a, $J_{H8a-H8b}$=12.5 Hz); 4.70 (d, 1H, H1, $J_{H1-H2}$=7.9 Hz); 4.66 (d, 1H, H8b, $J_{H8b-H8a}$=12.6 Hz); 4.42 (dd, 1H, H6a, $J_{H6a-H5}$=5.0 Hz, $J_{H6a-H6b}$=10.5 Hz); 3.99 (t, 1H, H3, $J_{H3-H2}$=$J_{H3-H4}$=9.2 Hz); 3.85 (t, 1H, H6b, $J_{H6b-H5}$=$J_{H6b-H6a}$=10.3 Hz); 3.68 (t, 1H, H4, $J_{H4-H3}$=$J_{H4-H5}$=9.4 Hz); 3.49 (ddd, 1H, H5, $J_{H5-H4}$=$J_{H5-H6b}$=9.7 Hz, $J_{H5-H6a}$=5.1 Hz,); 2.84 (s, 1H, OH).

EXAMPLE 6

Synthesis of a Disaccharide According to the Invention

This Example illustrates the interest of the method according to the invention for the preparation of a disaccharide by a reaction of coupling between two monosaccharides, it being possible for the disaccharide obtained itself to act as a precursor of a disaccharide glycosyl acceptor (see Example 7) for the synthesis of a trisaccharide (see Example 8).

Synthesis of Benzyl 2-O-benzoyl-4,6-O-benzylidene-3-O (2-methylnaphthyl)-β-D-glucopyranosyl-(1→3)-2-O-benzoyl-4,6-O-benzylidene-β-D-glucopyranoside.

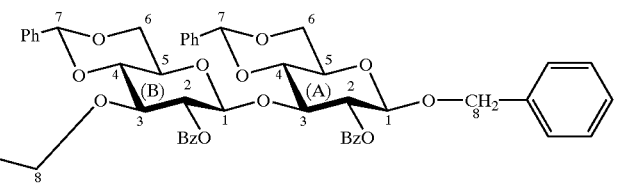

8.02 g (1.1 eq.) of ethyl 2-O-benzoyl-4,6-O-benzylidene-3-O-2-methylnaphthyl)-1-thio-β-D-glucopyranoside prepared in Example 4 (M=556.7) and 6.06 g (1 eq.) of benzyl 2-O-benzoyl-4,6-O-benzylidene-β-D-glucopyranoside prepared in Example 5 (M=462.5) are dissolved in 70 mL of anhydrous dichloromethane in the presence of 2 g of 4 Å molecular seives at 0° C. 3.24 g (1.1 to 1.2 eq.) of N-iodosuccinimide (NIS) and 296 μL (0.1 eq.) of triethylsilyl trifluoromethanesulphonate (TESOTf) are then added thereto. After 50 min of reaction, the medium is neutralised with triethylamine, filtered and then washed with a 10% sodium thiosulphate solution and then with water. After drying and evaporation of the organic phase, the product expected is purified by chromatography over silica gel [flash; eluent: toluene/ethyl acetate (95/5; v/v)]. 10.36 g of benzyl 2-O-benzoyl-4,6-O-benzylidene-3-O-(2-methylnaphthyl)-β-D-glucopyranosyl-(1→3)-2-O-benzoyl-4,6-O-benzylidene-β-D-glucopyranoside (M=957.1) are thus obtained.

TLC: Rf=0.6 [toluene/ethyl acetate (8/2; v/v)]. White solid. Yield (%)=83%

$^{13}$C (CDCl$_3$, 100 MHz): 164.74, 164.58 (C=O); 137.32, 137.19, 136.65, 135.33, 133.04, 132.96, 132.85, 132.72 (8 C quat. arom.); 129.82–125.67 (C arom.); 101.50, 101.08 (C7A, C7B); 100.58 (C1B); 99.62 (C1A); 80.89 (C4B); 79.30 (C4A); 78.22 (C3B); 77.79 (C3A); 73.69 (C2B); 73.52, 73.49 (C2A, C8B); 70.28 (C8A); 68.77, 68.73 (C6A, C6B); 66.48 (C5A); 66.00 (C5B).

$^1$H NMR (CDCl$_3$, 400 MHz): 7.74–7.02 (m, 32H, H arom.); 5.53 (s, 1H, H7A or H7B); 5.34 (s, 1H, H7A or H7B); 5.31 (dd, 1H, H2A, $J_{H2A\text{-}H1A}$=7.7 Hz, $J_{H2A\text{-}H3A}$=9.2 Hz); 5.28 (t, 1H, H2B, $J_{H2B\text{-}H1B}$=$J_{H2B\text{-}H3B}$=7.4 Hz); 4.85 (d, 1H, H1B, $J_{H1B\text{-}H2B}$=7.0 Hz); 4.84 (d, 1H, H8aB, $J_{H8aB\text{-}H8bB}$=12.4 Hz); 4.74 (d, 1H, H8bB, $J_{H8bB\text{-}H8aB}$=12.2 Hz); 4.74 (d, 1H, H8aA, $J_{H8aA\text{-}H8bA}$=12.2 Hz); 4.56 (d, 1H, H1A, $J_{H1A\text{-}H2A}$=7.6 Hz); 4.50 (d, 1H, H8bA, $J_{H8bA\text{-}H8aA}$=12.6 Hz); 4.36 (dd, 1H, H6aA, $J_{H6aA\text{-}H5A}$=4.9 Hz, $J_{H6aA\text{-}H6bA}$=10.5 Hz); 4.16 (dd, 1H, H6aB, $J_{H6aB\text{-}H5B}$=4.9 Hz, $J_{H6aB\text{-}H6bB}$=10.4 Hz); 4.11 (t, 1H, H3A, $J_{H3A\text{-}H2A}$=$J_{H3A\text{-}H4A}$=8.8 Hz); 3.90 (t, 1H, H4B, $J_{H4B\text{-}H3B}$=$J_{H4B\text{-}H5B}$=9.4 Hz); 3.84 (t, 1H, H4A, $J_{H4A\text{-}H3A}$=$J_{H4A\text{-}H5A}$=9.3 Hz); 3.80 (dd, 1H, H6bA, $J_{H6bA\text{-}H5A}$=$J_{H6bA\text{-}H6aA}$=10.3 Hz); 3.74 (dd, 1H, H3B, $J_{H3B\text{-}H2B}$=7.9 Hz, $J_{H3B\text{-}H4B}$=8.9 Hz); 3.68 (t, 1H, H6bB, $J_{H6bB\text{-}H5B}$=$J_{H6bB\text{-}H6aB}$=10.3 Hz); 3.49 (ddd, 1H, H5A, $J_{H5A\text{-}H4A}$=$J_{H5A\text{-}H6bA}$=9.7 Hz, $J_{H5A\text{-}H6aA}$=4.9 Hz,); 3.37 (ddd, 1H, H5B, $J_{H5B\text{-}H4}$=$J_{H5B\text{-}H6bA}$=9.7 Hz, $J_{H5B\text{-}H6aB}$=4.9 Hz).

EXAMPLE 7

Synthesis of a Disaccharide Glycosyl Acceptor According to the Invention

Synthesis of Benzyl 2-O-benzoyl-4,6-O-benzylidene-β-D-glucopyranosyl-(1→3)-2-O-benzoyl-4,6-O-benzylidene-β-D-glucopyranoside.

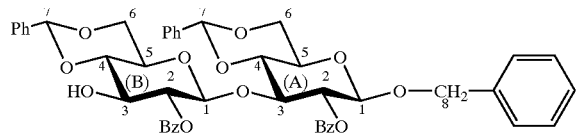

After dissolution of 2.17 g (1 eq.) of benzyl 2-O-benzoyl-4,6-O-benzylidene-3-O-(2-methylnaphthyl)-β-D-glucopyranosyl-(1→3)-2-O-benzoyl-4,6-O-benzylidene-β-D-glucopyranoside of (M=957.1) in 43 mL of a dichloromethane/methanol (4/1; v/v) mixture, we add 1.54 g (3 eq.) of 2,3-dichloro-5,6-dicyano-1,4-benzoquinone (DDQ) and the whole is left to evolve for 4 hours 30 minutes at ambient temperature. The medium is then diluted with dichloromethane, washed with a 5% sodium bicarbonate solution and then with water. The organic phase is dried, evaporated and the product sought after is obtained after purification over silica gel [flash; eluent: toluene/ethyl acetate (9/1; v/v)]. 1.46 g of benzyl 2-O-benzoyl-4,6-O-benzylidene-β-D-glucopyranosyl-(1→3)-2-O-benzoyl-4,6-O-benzylidene-β-D-glucopyranoside (M=815.9) are thus collected.

TLC: Rf=0.4 [toluene/ethyl acetate (8/2; v/v)]. White solid. Yield (%)=79%

$^{13}$C NMR (CDCl$_3$, 100 MHz): 165.64, 164.67 (C=O); 137.17, 136.97, 136.64, 133.10, 133.00 (5 C quat. arom.); 129.81–126.15 (C arom.); 101.69, 101.49 (C7A, C7B); 100.38 (C1B); 99.58 (C1A); 80.54 (C4B); 79.31 (C4A); 78.00 (C3A); 75.27 (C2B); 73.51 (C2A); 72.60 (C3B); 70.33 (C8A); 68.77 (C6A); 68.65 (C6B); 66.46 (C5A); 66.05 (C5B).

$^1$H NMR (CDCl$_3$, 400 MHz): 7.70–6.96 (m, 25H, H arom.); 5.47 (s, 1H, H7A or H7B); 5.27 (s, 1H, H7A or H7B); 5.25 (t, 1H, H2A, $J_{H2A\text{-}H1A}$, =$J_{H2A\text{-}H3A}$=7.6 Hz); 5.03 (dd, 1H, H2B, $J_{H2B\text{-}H1B}$=7.4 Hz, $J_{H2B\text{-}H3B}$=8.0 Hz); 4.83 (d, 1H, H1B, $J_{H1B\text{-}H2B}$=7.2 Hz); 4.69 (d, 1H, H8aA, $J_{H8aA\text{-}H8bA}$=12.5 Hz); 4.52 (d, 1H, H1A, $J_{H1A\text{-}H2A}$=7.5 Hz); 4.44 (d, 1H, H8bA, $J_{H8bA\text{-}H8aA}$=12.6 Hz); 4.30 (dd, 1H, H6aA, $J_{H6aA\text{-}H5A}$=4.8 Hz, $J_{H6aA\text{-}H6bA}$=10.4 Hz); 4.10 (dd, 1H, H6aB, $J_{H6aB\text{-}H5B}$=4.8 Hz, $J_{H6aB\text{-}H6bB}$=10.5 Hz); 4.08 (t, 1H, H3A, $J_{H3A\text{-}H2A}$=$J_{H3A\text{-}H4A}$=8.7 Hz); 3.77 (t, 1H, H4A, $J_{H4A\text{-}H3A}$=$J_{H4A\text{-}H5A}$=9.3 Hz); 3.76 (t, 1H, H3B, $J_{H3B\text{-}H2B}$=$J_{H3B\text{-}H4B}$=10.2 Hz); 3.73 (t, 1H, H6bA, $J_{H6bA\text{-}H5A}$=$J_{H6bA\text{-}H6aA}$=10.3 Hz); 3.60 (t, 1H, H6bB, $J_{H6bB\text{-}H5B}$=$J_{H6bB\text{-}H6aB}$=10.3 Hz); 3.57 (t, 1H, H4B, $J_{H4B\text{-}H3B}$=$J_{H4B\text{-}H5B}$=9.4 Hz); 3.44 (ddd, 1H, H5A, $J_{H5A\text{-}H4A}$=$J_{H5A\text{-}H6bA}$=9.7 Hz, $J_{H5A\text{-}H6aA}$=4.8 Hz,); 3.28 (ddd, 1H, H5B, $J_{H5B\text{-}H4B}$=$J_{H5B\text{-}H6bB}$=9.7 Hz, $J_{H5B\text{-}H6aB}$=4.9 Hz,); 2.55 (s, 1H, OH).

EXAMPLE 8

Synthesis of a Trisaccharide According to the Invention

This Example illustrates the interest of the method according to the present invention for the preparation of a trisaccharide by a reaction of coupling between a monosaccharide and a disaccharide, it being possible for the trisaccharide obtained itself to act as a glycosyl acceptor precursor (see Example 9) for the synthesis of a tetrasaccharide (see Example 10).

Synthesis of Benzyl 2-O-benzoyl-4,6-O-benzylidene-3-O-(2-methylnaphthyl)-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranoside.

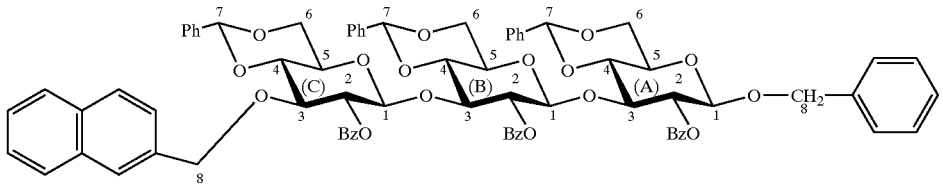

5.03 g (1.1 eq.) of ethyl 2-O-benzoyl-4,6-O-benzylidene-3-O-2-methylnaphthyl)-1-thio-β-D-glucopyranoside prepared in Example 4 (M=556.7) and 6.70 g (1 eq.) of benzyl 2-O-benzoyl-4,6-O-benzylidene-β-D-glucopyranosyl-(1→3)-2-O-benzoyl-4,6-O-benzylidene-β-D-glucopyranoside prepared in Example 7 (M=815.9) are dissolved in 100 mL of anhydrous dichloromethane in the presence of 10 g of 4 Å molecular sieves at 0° C. 2.03 g of NIS (1.1 to 1.2 eq.) and 190 µL of TESOTf (0.1 eq.) are then added thereto. After 50 min of reaction, the medium is neutralised with triethylamine, filtered and then washed with a 10% sodium thiosulphate solution and then with water. After drying and evaporation of the organic phase, the product expected is purified by chromatography over silica gel [flash; eluent: toluene/ethyl acetate (95/5 and then 9/1; v/v). 9.28 g of benzyl 2-O-benzoyl-4,6-O-benzylidene-3-O-methylnaphthyl-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranoside (M=1310.5) are thus isolated.

TLC: Rf=0.5 [toluene/ethyl acetate (17/3; v/v)]. White solid. Yield (%)=86%

$^{13}$C NMR (CDCl$_3$, 100 MHz): 165.12, 164.77, 164.53 (3 C=O); 137.40, 137.36, 137.20, 136.78, 135.42, 133.43, 133.16 (2 C), 133.09, 132.90 (10 C quat. arom.); 129.93–125.37 (C arom.); 101.94, 101.22, 100.56 (C7A,B,C); 99.49 (C1A); 98.32 (C1C); 97.90 (C1B); 81.38 (C4C); 78.67 (C4A); 78.19 (C3C); 77.61 (C4B); 76.22 (C3B); 74.31 (C2A); 74.11 (C3A); 73.87 (C8C); 73.28 (C2C); 72.58 (C2B); 70.22 (C8A); 68.81 (C6B); 68.77 (C6C), 68.67 (C6A); 66.49 (C5A); 66.14 (C5C); 65.37 (C5B).

$^1$H NMR (CDCl$_3$, 400 MHz): 7.90–7.05 (m, 42H, H arom.); 5.47 (s, 1H, H7); 5.46 (s, 1H, H7); 5.34 (t, 1H, H2C, $J_{H2C-H1C}=J_{H2C-H3C}=7.8$ Hz); 5.08 (t, 1H, H2B, $J_{H2B-H1B}=J_{H2B-H3B}=4.2$ Hz); 5.06 (d, 1H, H1C, $J_{H1C-H2C}=7.4$ Hz); 4.91 (d, 1H, H8aC, $J_{H8aC-H8bC}=12.3$ Hz); 4.86 (d, 1H, H1B, $J_{H1B-H2B}=4.4$ Hz); 4.86 (dd, 1H, H2A, $J_{H2A-H1A}=8.0$ Hz, $J_{H2A-H3A}=8.6$ Hz); 4.80 (d, 1H, H8bC, $J_{H8bC-H8aC}=12.4$ Hz); 4.75 (d, 1H, H8aA, $J_{H8aA-H8bA}=12.5$ Hz); 4.57 (s, 1H, H7); 4.49 (d, 1H, H8bA, $J_{H8bA-H8aA}=12.6$ Hz); 4.45 (d, 1H, H1A, $J_{H1A-H2A}=7.7$ Hz); 4.31 (dd, 1H, H6aA, $J_{H6aA-H5A}=4.8$ Hz, $J_{H6aA-H6bA}=10.4$ Hz); 4.22 (dd, 1H, H6aC, $J_{H6aC-H5C}=4.9$ Hz, $J_{H6aC-H6bC}=10.4$ Hz); 4.11 (dd, 1H, H6aB, $J_{H6aB-H5B}=3.5$ Hz, $J_{H6aB-H6bB}=8.9$ Hz); 4.07 (t, 1H, H3A, $J_{H3A-H2A}=J_{H3A-H4A}=9.1$ Hz); 4.07 (dd, 1H, H4B, $J_{H4B-H3B}=8.1$ Hz, $J_{H4B-H5B}=9.6$ Hz); 3.97 (dd, 1H, H3B, $J_{H3B-H2B}=3.9$ Hz, $J_{H3B-H4B}=8.1$ Hz); 3.91 (t, 1H, H4C, $J_{H4C-H3C}=J_{H4C-H5C}=$ 9.1 Hz); 3.85 (dd, 1H, H3C, $J_{H3C-H2C}=8.1$ Hz, $J_{H3C-H4C}=9.0$ Hz); 3.72 (dd, 1H, H6bC, $J_{H6bC-H5C}=J_{H6bC-H6aC}=10.3$ Hz); 3.64 (t, 1H, H6bA, $J_{H6bA-H5A}=J_{H6bA-H6aA}=10.2$ Hz); 3.55 (ddd, 1H, H5B, $J_{H5B-H4B}=J_{H5B-H6bB}=10.0$ Hz, $J_{H5B-H6aB}=4.3$ Hz,); 3.52 (t, 1H, H6bB, $J_{H6bB-H5B}=J_{H6bB-H6aB}=9.3$ Hz); 3.50 (ddd, 1H, H5C, $J_{H5C-H4C}=J_{H5C-H6bC}=9.8$ Hz, $J_{H5C-H6aC}=3.8$ Hz,); 3.37 (ddd, 1H, H5A, $J_{H5A-H4A}=J_{H5A-H6bA}=9.8$ Hz, $J_{H5A-H6aA}=4.9$ Hz,); 3.18 (t, 1H, H4A, $J_{H4A-H3A}=J_{H4A-H5A}=9.4$ Hz).

EXAMPLE 9

Synthesis of a Trisaccharide Glycosyl Acceptor According to the Invention

Synthesis of Benzyl 2-O-benzoyl-4,6-O-benzylidene-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranoside.

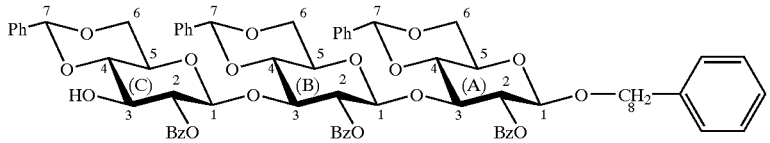

After dissolution of 6.21 g (1 eq.) of benzyl 2-O-benzoyl-4,6-O-benzylidene-3-O-(2-methylnaphthyl)-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranoside (M=1310.5) in 125 mL of a dichloromethane/methanol (4/1; v/v) mixture, we add 3.23 g (3 eq.) of DDQ and the whole is left to evolve for 7 hours at ambient temperature. The medium is then diluted with dichloromethane, washed with a 5% sodium bicarbonate solution and then with water. The organic phase is dried, evaporated and the product sought after is obtained after purification over silica gel [flash; eluent: toluene/ethyl acetate (9/1 and then 17/3; v/v)]. 8.89 g of benzyl 2-O-benzoyl-4,6-O-benzylidene-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranoside (M=1170.3) are thus obtained.

TLC: Rf=0.3 [toluene/ethyl acetate (17/3; v/v)]. White solid. Yield (%)=78%

$^{13}$C NMR (CDCl$_3$, 100 MHz): 165.87, 164.81, 164.58 (3 C=O); 137.32, 137.18, 137.03, 136.75, 133.64, 133.23, 133.20 (7 C quat. arom.); 130.06–125.36 (C arom.); 101.96, 101.84, 100.57 (C7A,B,C); 99.48 (C1A); 98.18 (C1C); 98.03 (C1B); 80.85 (C4C); 78.72 (C4A); 77.64 (C4B); 76.31 (C3B); 74.73 (C2C); 74.40 (C3A); 74.28 (C2A); 72.66 (C2B); 72.54 (C3C); 70.26 (C8A); 68.78 (C6B); 68.67 (C6A, C6C), 66.48 (C5A); 66.09 (C5C); 65.40 (C5B).

$^1$H NMR (CDCl$_3$, 400 MHz): 8.02–7.06 (m, 35H, H arom.); 5.47 (s, 1H, H7); 5.42 (s, 1H, H7); 5.20 (dd, 1H, H2C, $J_{H2C-H1C}$=7.6 Hz, $J_{H2C-H3C}$=8.4 Hz); 5.13 (t, 1H, H2B, $J_{H2B-H1B}$=$J_{H2B-H3B}$=4.2 Hz); 5.11 (d, 1H, H1C, $J_{H1C-H2C}$= 7.5 Hz); 4.95 (dd, 1H, H2A, $J_{H2A-H1A}$=8.0 Hz, $J_{H2A-H3A}$=8.6 Hz); 4.90 (d, 1H, H1B, $J_{H1B-H2B}$=4.4 Hz); 4.76 (d, 1H, H8aA, $J_{H8aA-H8bA}$=12.6 Hz); 4.62 (s, 1H, H7); 4.32 (d, 1H, H8bA, $J_{H8bA-H8aA}$=12.6 Hz); 4.47 (d, 1H, H1A, $J_{H1A-H2A}$= 7.8 Hz); 4.31 (dd, 1H, H6aA, $J_{H6aA-H5A}$=4.8 Hz, $J_{H6aA-H6bA}$= 10.4 Hz); 4.22 (dd, 1H, H6aC, $J_{H6aC-H5C}$=4.8 Hz, $J_{H6aC-H6bC}$=10.4 Hz); 4.12 (dd, 1H, H6aB, $J_{H6aB-H5B}$=3.3 Hz, $J_{H6aB-H6bB}$=8.8 Hz); 4.09 (t, 1H, H3A, $J_{H3A-H2A}$= $J_{H3A-H4A}$=9.0 Hz); 4.07 (dd, 1H, H4B, $J_{H4B-H3B}$=$J_{H4B-H5B}$= 8.9 Hz); 4.01 (dd, 1H, H3B, $J_{H3B-H2B}$=3.8 Hz, $J_{H3B-H4B}$=8.1 Hz); 3.96 (ddd, 1H, H3C, $J_{H3C-H2C}$=$J_{H3C-H4C}$=8.7 Hz, $J_{H3C-OH}$=3.6 Hz); 3.69 (dd, 1H, H6bC, $J_{H6bC-H5C}$= $J_{H6bC-H6aC}$=10.2 Hz); 3.67 (t, 1H, H4C, $J_{H4C-H3C}$= $J_{H4C-H5C}$=9.4 Hz); 3.65 (t, 1H, H6bA, $J_{H6bA-H5A}$=$J_{H6bA-H6aA}$=10.6 Hz); 3.56 (ddd, 1H, H5B, $J_{H5B-H4B}$=$J_{H5B-H6bB}$= 9.7 Hz, $J_{H5B-H6aB}$=4.1 Hz,); 3.55–3.47 (m, 2H, H6bB, H5C); 3.38 (ddd, 1H, H5A, $J_{H5A-H4A}$=$J_{H5A-H6bA}$=10.0 Hz, $J_{H5A-H6aA}$=4.9 Hz,); 3.21 (t, 1H, H4A, $J_{H4A-H3A}$=$J_{H4A-H5A}$= 9.4 Hz); 2.64 (d, 1H, OH, $J_{OH-H3C}$=3.7 Hz).

EXAMPLE 10

Synthesis of a Tetrasaccharide According to the Invention

This Example illustrates the interest of the method according to the present invention for the preparation of a tetrasaccharide by a reaction of coupling between a monosaccharide and a trisaccharide, it being possible for the tetrasaccharide obtained itself to act as a tetrasaccharide glycosyl acceptor precursor (see Example 11) for the synthesis of a pentasaccharide, and so forth.

Synthesis of Benzyl 2-O-benzoyl-4,6-O-benzylidene-3-O-(2-methylnaphthyl)-β-D-glucopyranosyl-(1→3)-2-O-benzoyl-4,6-O-benzylidene-β-D-glucopyranosyl-(1→3)-O-benzoyl-4,6-O-benzylidene-β-D-glucopyranosyl-(1→3)-2-O-benzoyl-4,6-O-benzylidene-β-D-glucopyranoside.

3.23 g (1.1 eq.) of ethyl 2-O-benzoyl-4,6-O-benzylidene-3-O-2-methylnaphthyl)-1-thio-β-D-glucopyranoside prepared in Example 4 (M=556.7) and 6.17 g (1 eq.) of benzyl 2-O-benzoyl-4,6-O-benzylidene-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranoside prepared in Example 9 (M=1170.3) are dissolved in 100 mL of anhydrous dichloromethane in the presence of 10 g of 4 Å molecular sieves at 0° C. 1.42 g (1.2 eq.) of NIS and 100 μL (0.1 eq.) of trimethylsilyl trifluoromethanesulphonate (TMSOTf) are then added thereto. After 1 h of reaction, the medium is neutralised with triethylamine, filtered and then washed with a 10% sodium thiosulphate solution and then with water. After drying and evaporation of the organic phase, the product expected is purified by chromatography over silica gel [flash; eluent: toluene/ethyl acetate (95/5 and then 925/75 and then 9/1; v/v). 7.70 g of benzyl 2-O-benzoyl-4,6-O-benzylidene-3-O-(2-methylnaphthyl)-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranoside (M=1664.9) are thus collected.

TLC: Rf=0.5 [toluene/ethyl acetate (8/2; v/v)]. White solid. Yield (%)=88%

$^{13}$C NMR (CDCl$_3$, 100 MHz): 165.05, 164.68, 164.58, 164.55 (4 C=O); 137.36, 137.32, 137.24, 137.17, 136.69, 135.41, 133.41, 133.36, 133.09, 133.05 (2 C), 132.85 (12 C quat. arom.); 129.80–125.33 (C arom.); 101.82, 101.16, 101.08, 100.77 (C7A,B,C,D); 99.49 (C1A); 99.04 (C1D); 98.42 (C1B); 96.94 (C1C); 81.28 (C4D); 78.82 (C4A); 78.28, 78.16 (C3D, C4C); 77.41 (C4B); 76.90 (C3C); 75.07 (C3A); 74.16 (C3B); 73.96 (C2A); 73.77 (C8D); 73.47 (C2B); 73.39 (C2D); 72.54 (C2C); 70.24 (C8A); 68.71, 68.67 (C6A,B,C,D); 66.44, 66.04, 65.52 (C5A,B,C,D).

$^1$H NMR (CDCl$_3$, 400 MHz): 7.78–7.04 (m, 52H, H arom.); 5.53 (s, 1H, H7); 5.43 (s, 1H, H7); 5.33 (t, 1H, H2D, $J_{H2D-H1D}$=$J_{H2D-H3D}$=7.8 Hz); 5.12 (t, 1H, H2C, $J_{H2C-H1C}$= $J_{H2C-H3C}$=5.3 Hz); 4.98 (d, 1H, H1D, $J_{H1D-H2D}$=7.4 Hz); 4.98 (dd, 1H, H2A, $J_{H2A-H1A}$=8.0 Hz, $J_{H2A-H3A}$=8.5 Hz); ); 4.95 (d, 1H, H1C, $J_{H1C-H2C}$=5.4 Hz); 4.89 (d, 1H, H8aD, $J_{H8aD-H8bD}$=12.5 Hz); 4.82 (s, 1H, H7); 4.79 (d, 1H, H8bD, $J_{H8bD-H8aD}$=11.8 Hz); 4.76 (d, 1H, H8aA, $J_{H8aA-H8bA}$=11.4 Hz); 4.75 (d, 1H, H1B, $J_{H1B-H2B}$=3.1 Hz); 4.75 (m, 1H, H$_2$B); 4.74 (s, 1H, H7); 4.50 (d, 1H, H8bA, $J_{H8bA-H8aA}$=12.6 Hz); 4.47 (d, 1H, H1A, $J_{H1A-H2A}$=7.8 Hz); 4.34 (dd, 1H, H6a, $J_{H6a-H5}$=4.6 Hz, $J_{H6a-H6b}$=10.3 Hz); 4.19 (dd, 1H, H6a, $J_{H6a-H5}$=4.9 Hz, $J_{H6a-H6b}$=10.4 Hz); 4.12–4.09 (m, 2H, H6); 4.04 (t, 1H, H3A, $J_{H3A-H2A}$=$J_{H3A-H4A}$=8.7 Hz); 4.03–4.00 (m, 1H, H3C); 3.95 (t, 1H, H4C, $J_{H4C-H3C}$=$J_{H4C-H5C}$=8.8 Hz); 3.92–3.89 (m, 1H, H3B); 3.87 (dd, 1H, H4D, $J_{H4D-H3D}$=9.3 Hz, $J_{H4D-H5D}$=8.7 Hz); 3.82 (dd, 1H, H3D,

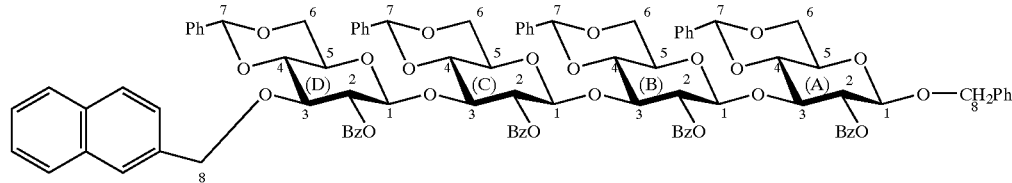

$J_{H3D-H2D}$=8.0 Hz, $J_{H3D-H4D}$=9.1 Hz); 3.75–3.68 (m, 2H, H6); 3.59–3.37 (m, 5H, H4B, 4 H5, 2 H6); 3.35 (t, 1H, H4A, $J_{H4A-H3A}$=$J_{H4A-H5A}$=9.2 Hz).

EXAMPLE 11

Synthesis of a Tetrasaccharide Acceptor According to the Invention

Synthesis of Benzyl 2-O-benzoyl-4,6-O-benzylidene-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranoside

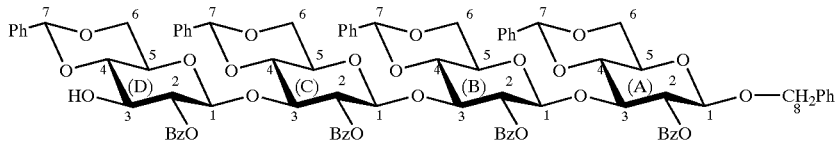

After dissolution of 3.79 g (1 eq.) of benzyl 2-O-benzoyl-4,6-O-benzylidene-3-O-methylnaphthyl-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranoside (M=1664.9) in 55 mL of a dichloromethane/methanol (4/1; v/v) mixture, we add 1.55 g (3 eq.) of DDQ and the whole is left to evolve for 7 hours 30 minutes at ambient temperature. The medium is then diluted with dichloromethane, washed with a 5% sodium bicarbonate solution and then with water. The organic phase is dried, evaporated and the product sought after is obtained after purification over silica gel [flash; eluent: toluene/ethyl acetate (17/3; v/v)]. 2.78 g of benzyl 2-O-benzoyl-4,6-O-benzylidene-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranosyl-(1→3)-2-O-benzoyl-4,6-O-benzylidene-β-D-glucopyranoside (M=1523.7) are thus isolated.

TLC: Rf=0.3 [toluene/ethyl acetate (8/2; v/v)]. White solid. Yield (%)=80%

$^{13}$C NMR (CDCl$_3$, 100 MHz): 165.80, 164.66, 164.61, 164.59 (4 C=O); 137.28, 137.20, 137.13, 137.00, 136.65, 133.62, 133.42, 133.10, 133.06 (9 C quat. arom.); 129.87–125.31 (C arom.); 101.80, 101.71, 101.10, 100.71 (C7A,B,C,D); 99.46 (C1A); 98.76 (C1D); 98.45 (C1B); 96.98 (C1C); 80.73 (C4D); 78.80 (C4A); 78.20 (C4C); 77.42 (C4B); 76.84 (C3C); 75.14 (C3A); 74.75 (C2D); 74.30 (C3B); 73.93 (C2A); 73.47 (C2B); 72.53 (C2C); 72.38 (C3D); 70.22 (C8A); 68.62 (C6A,B,C,D); 66.41, 66.00, 65.50 (C5A,B,C,D).

$^1$H NMR (CDCl$_3$, 400 MHz): 7.91–7.04 (m, 45H, H arom.); 5.51 (s, 1H, H7); 5.39 (s, 1H, H7); 5.16 (dd, 1H, H2D, $J_{H2D-H1D}$=7.6 Hz, $J_{H2D-H3D}$=8.4 Hz); 5.15 (t, 1H, H2C, $J_{H2C-H1C}$=$J_{H2C-H3C}$=5.3 Hz); 5.02 (d, 1H, H1D, $J_{H1D-H2D}$=7.6 Hz); 4.99 (dd, 1H, H2A, $J_{H2A-H1A}$=8.0 Hz, $J_{H2A-H3A}$=9.6 Hz); 4.97 (d, 1H, H1C, $J_{H1C-H2C}$=5.3 Hz); 4.83 (s, 1H, H7); 4.82 (t, 1H, H2B, $J_{H2B-H1B}$=$J_{H2B-H3B}$=5.2 Hz); 4.76 (d, 1H, H1B, $J_{H1B-H2B}$=5.6 Hz); 4.75 (d, 1H, H8aA, $J_{H8aA-H8bA}$=10.8 Hz); 4.74 (s, 1H, H7); 4.50 (d, 1H, H8bA, $J_{H8bA-H8aA}$=13.4 Hz); 4.47 (d, 1H, H1A, $J_{H1A-H2A}$=7.9 Hz); 4.34 (dd, 1H, H6a, $J_{H6a-H5}$=4.6 Hz, $J_{H6a-H6b}$=10.4 Hz); 4.18 (dd, 1H, H6a, $J_{H6a-H5}$=4.9 Hz, $J_{H6a-H6b}$=10.4 Hz); 4.12–4.09 (m, 2H, H6a); 4.05 (dd, 1H, H3C, $J_{H3C-H2C}$=4.9 Hz, $J_{H3C-H4C}$=8.3 Hz); 4.04 (t, 1H, H3A, $J_{H3A-H2A}$=$J_{H3A-H4A}$=8.8 Hz); 3.95 (dd, 1H, H4C, $J_{H4C-H3C}$8.7 Hz, $J_{H4C-H5C}$=9.1 Hz); ); 3.91 (dd, 1H, H3B, $J_{H3B-H2B}$=5.6 Hz, $J_{H3B-H4B}$=8.5 Hz); 3.89 (dddd, 1H, H3D, $J_{H3D-H2D}$=$J_{H3D-H4D}$=8.9 Hz, $J_{H3D-OH}$=4.0 Hz); 3.72 (t, 1H, H6b, $J_{H6b-H5}$=$J_{H6b-H6a}$=9.9 Hz); 3.67 (t, 1H, H6b, $J_{H6b-H5}$=$J_{H6b-H6a}$=10.1 Hz); 3.60 (t, 1H, H4D, $J_{H4D-H3D}$=$J_{H4D-H5D}$=9.4 Hz); 3.58–3.54 (m, 1H, H5C); 3.51 (t, 1H, H6b, $J_{H6b-H5}$=$J_{H6b-H6a}$=10.0 Hz); 3.47–3.37 (m, 5H, H4B, H5A, B,D, H6b); 3.35 (t, 1H, H4A, $J_{H4A-H3A}$=$J_{H4A-H5A}$=9.2 Hz); 2.73 (d, 1H, OH, $J_{OH-H3C}$=3.8 Hz).

EXAMPLE 12

Other Example of Synthesis of a Glycosyl Donor Synthon of General Formula (Ia) According to the Invention It will be possible for the person skilled in the art to easily determine the most appropriate reaction conditions of the preparation of ethyl 2-O-acetyl-3-O-allyl-4,6-di-O-benzyl-1-thio-β-D-glucopyranoside according to the steps [1] to [5], [6] to and then [8] notably by following the teaching of the Examples described above.

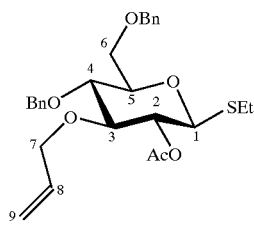

M=486 g/mol.

TLC: Rf=0.6 [petroleum ether/ethyl acetate (8/2; v/v)]. Colourless oil.

$^{13}$C NMR (CDCl$_3$, 100 MHz) □ (ppm): 169.68 (C=O); 138.21, 137.97 (C quat. arom.); 134.74 (C8); 128.52, 128.44, 128.17, 127.96, 127.78, 127.68 (C arom.); 117.02 (C9) 84.17 (C3); 83.39 (C1); 79.49 (C5); 77.66 (C4); 75.17 (CH$_2$—Ar); 74.12 (C7); 73.51 (CH$_2$—Ar); 71.83 (C2); 68.92 (C6); 23.85 (S—CH$_2$); 21.18 (CH3-CO); 14.97 (S—CH$_2$—CH$_3$).

$^1$H NMR (CDCl$_3$, 400 MHz) □ (ppm): 7.34–7.21 (m, 10H, H arom.); 5.87 (ddt, 1H, H8, $J_{H8-H7a}$=$J_{H8-H7b}$=5.7 Hz, $J_{H8-H9a}$=17.2 Hz, $J_{H8-H9b}$=10.4 Hz); 5.24 (ddt, 1H, H9a, $J_{H9a-H7}$=1.6 Hz, $J_{H9a-H8}$=17.2 Hz, $J_{H9a-H9b}$=1.7 Hz); 5.15 (ddt, 1H, H9b, $J_{H9b-H7}$=1.2 Hz, $J_{H9b-H8}$=10.4 Hz, $J_{H9b-H9a}$=1.5 Hz); 4.97 (dd, 1H, H2, $J_{H2-H1}$=9.9 Hz, $J_{H2-H3}$=9.2 Hz); 4.80 (d, 1H, CH$_2$—Ar, $^2$J=10.7 Hz); 4.60 (d, 1H, CH$_2$—Ar, $^2$J=12.2 Hz); 4.56 (d, 1H, CH$_2$—Ar, $^2$J=10.8 Hz); 4.54 (d, 1H, CH$_2$—Ar, $^2$J=12.1 Hz); 4.35 (d, 1H, H1, $J_{H1-H2}$=10.0 Hz); 4.27 (ddt, 1H, H7a, $J_{H7a-H7b}$=12.6 Hz, $J_{H7a-H8}$=5.6 Hz, $J_{H7a-H9}$=1.4 Hz); 4.16 (ddt, 1H, H7b, $J_{H7b-H7a}$=12.6 Hz, $J_{H7b-H8}$=5.9 Hz, $J_{H7b-H9}$=1.4 Hz); 3.74 (dd, 1H, H6a, $J_{H6a-H5}$=2.0 Hz, $J_{H6a-H6b}$=11.1 Hz); 3.69 (dd, 1H, H6b, $J_{H6b-H5}$=4.5 Hz, $J_{H6b-H6a}$=11.0 Hz); 3.63 (t, 1H, H4, $J_{H4-H3}$=$J_{H4-H5}$=9.4 Hz); 3.54 (t, 1H, H3, $J_{H3-H2}$=$J_{H3-H4}$=9.0 Hz); 3.47 (ddd, 1H, H5, $J_{H5-H4}$=9.7 Hz, $J_{H5-H6a}$=1.9 Hz, $J_{H5-H6b}$=4.4 Hz); 2.69 (qd, 2H, S—CH$_2$CH$_3$, J=7.4 Hz, J=9.6 Hz); 2.11 (s, 3H, CH$_3$—CO); 1.26 (t, 3H, S—CH$_2$—CH$_3$, J=7.4 Hz).

EXAMPLE 13

Synthesis of a Synthon According to the Invention

This example illustrates the preparation of a synthon according to the invention which can be a glycosyl donor, or a glycosyl acceptor, by reaction with a more active donor, such as, for example, a trichloroacetimidate.

Synthesis of Ethyl 2-O-acetyl-4,6-di-O-benzyl-1-thio-β-D-glucopyranoside.

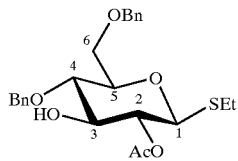

2.74 g (7.5 eq.) of Dabco and 450 mg (0.15 eq.) of Wilkinson's catalyst are added to 1.58 g of ethyl 2-O-acetyl-3-O-allyl-4,6-di-O-benzyl-1-thio-β-D-glucopyranoside (M=486) in 56 mL of an ethanol/toluene/water (8/3/1; v/v/v) mixture. The medium is refluxed for 2 hours and then concentrated. The mixture is taken up into dichloromethane, washed with iced water, with iced 5% HCl, iced 5% NaHCO$_3$, with iced water, dried (MgSO$_4$) and then put to dryness.

The residue is dissolved in 30 mL of an acetone/10% HCl aq. (19/1; v/v) mixture which is refluxed for 8 min, and then cooled to R.T., neutralised with 5% NaHCO$_3$ and concentrated. After taking up with dichloromethane and washings with water, the product is purified over silica gel [flash; eluent: toluene/ethyl acetate (9/1; v/v)] and 1 g of ethyl 2-O-acetyl-4,6-di-O-benzyl-1-thio-β-D-glucopyranoside (M=446) is isolated.

TLC: Rf=0.2 [toluene/ethyl acetate (9/1; v/v)]. Colourless oil. Yield (%)=69.

$^{13}$C NMR (CDCl$_3$, 100 MHz) □ (ppm): 170.62 (C=O); 138.11, 138.04 (C quat. arom.); 128.65, 128.44, 128.14, 128.10, 127.84, 127.73 (C arom.); 83.12 (C1); 79.20 (C5); 78.04 (C4); 76.92 (C3); 74.90 (CH$_2$—Ar); 73.56 ( CH$_2$—Ar); 72.54 (C2); 68.90 (C6); 23.97 (S—CH$_2$); 21.10 (CH3-CO); 15.00 (S—CH$_2$—CH$_3$).

$^1$H NMR (CDCl$_3$, 400 MHz) □ (ppm): 7.28–7.09 (m, 10H, H arom.); 4.80 (dd, 1H, H2, $J_{H2-H1}$=9.9 Hz, $J_{H2-H3}$=9.2 Hz); 4.68 (d, 1H, CH$_2$—Ar, $^2$J=11.2 Hz); 4.56 (d, 1H, CH$_2$—Ar, $^2$J=11.2 Hz); 4.56 (d, 1H, CH$_2$—Ar, $^2$J=12.0 Hz); 4.46 (d, 1H, CH$_2$—Ar, $^2$J=12.0 Hz); 4.31 (d, 1H, H1, $J_{H1-H2}$=10.0 Hz); 3.72–3.64 (m, 3H, H3, H6a, H6b); 3.51 (dd, 1H, H4, $J_{H4-H3}$=$J_{H4-H5}$=9.3 Hz); 3.40 (m, 1H, H5); 2.64 (qd, 2H, S—CH$_2$, J=7.4 Hz, J=9.6 Hz); 2.34 (d, 1H, OH, J=3.9 Hz); 2.06 (s, 3H, CH$_3$—CO); 1.20 (t, 1H, CH$_3$—CH$_2$—S, J=7.4 Hz).

EXAMPLE 14

Synthesis of a Glycosyl Donor Synthon of General Formula (Ib) According to the Invention
Synthesis of 2-O-acetyl-3-O-allyl-4,6-di-O-benzyl-α-D-glucopyranosyl trichloroacetimidate.

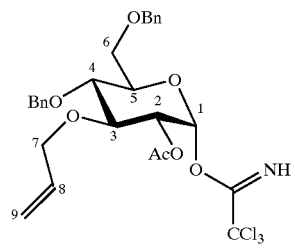

Step 14A 3.41 g (2 eq.) of N-bromosuccinimide are added to 4.68 g (1 eq.) of ethyl 2-O-acetyl-3-O-allyl-4,6-di-O-benzyl-1-thio-β-D-glucopyranoside (M=486) in 100 mL of an acetone/water (8/2; v/v) mixture. Once the reaction has stopped, the medium is diluted with dichloromethane, washed with a 5% sodium bicarbonate solution and then with water, dried (MgSO$_4$) and concentrated.

TLC: Rf=0.3 [petroleum ether/ethyl acetate (7/3; v/v)].

Step 14B

The residue obtained above (M=442) is then dissolved in 40 mL of anhydrous dichloromethane and 4.83 mL (5 eq.) of trichloroacetonitrile and 290 µL (0.2 eq.) dropwise of DBU are introduced. After 1 hour of reaction at ambient temperature, the medium is concentrated and purification over silica gel [flash; eluent: petroleum ether/ethyl acetate/triethylamine (85/15/1; v/v/v) enables isolating 4.38 g of 2-O-acetyl-3-O-allyl-4,6-di-O-benzyl-α-D-glucopyranosyl trichloro-acetimidate (M=586.5).

TLC: Rf=0.7 [petroleum ether/ethyl acetate (8/2; v/v)]. Colourless oil. Yield (%)=78.

$^{13}$C NMR (CDCl$_3$, 100 MHz) δ (ppm): 170.11 (C=O); 161.10 (C=NH); 137.92, 137.91 (C quat. arom.); 134.84 (C8); 128.55, 128.49, 128.30, 128.23, 128.17, 128.05, 128.00, 127.83 (C arom.); 116.92 (C9); 94.09 (C1); 79.30 (C3); 76.86 (C5); 75.52 (CH$_2$—Ar); 74.37 (C7); 73.58 ( CH$_2$—Ar); 73.45 (C4); 72.49 (C2); 67.94 (C6); 20.82 (CH3).

$^1$H NMR (CDCl$_3$, 400 MHz) □ (ppm): 8.57 (s, 1H, NH); 7.34–7.20 (m, 10H, H arom.); 6.52 (d, 1H, H1, $J_{H1-H2}$=3.6 Hz); 5.91 (ddt, 1H, H8, $J_{H8-H7a}$=$J_{H8-H7b}$=5.7 Hz, $J_{H8-H9a}$=17.2 Hz, $J_{H8-H9b}$=10.4 Hz); 5.27 (ddt, 1H, H9a, $J_{H9a-H7}$=1.6 Hz, $J_{H9a-H8}$=17.2 Hz, $J_{H9a-H9b}$=1.7 Hz); 5.16 (ddt, 1H, H9b, $J_{H9b-H7}$=1.2 Hz, $J_{H9b-H8}$=10.4 Hz, $J_{H9b-H9a}$=1.5 Hz); 5.02 (dd, 1H, H2, $J_{H2-H1}$=3.6 Hz, $J_{H2-H3}$=9.9 Hz); 4.84 (d, 1H, CH$_2$—Ar, $^2$J=10.6 Hz); 4.63 (d, 1H, CH$_2$—Ar, $^2$J=12.0 Hz); 4.56 (d, 1H, CH$_2$—Ar, $^2$J=10.5 Hz); 4.50 (d, 1H, CH$_2$—Ar, $^2$J=12.1 Hz); 4.33–4.32 (m, 2H, H7a, H7b); 3.97 (t, 2H, H3, H4, $J_{H3-H2}$=$J_{H3-H4}$=$J_{H4-H3}$=$J_{H4-H5}$=9.5 Hz); 3.84–3.78 (m, 2H, H5, H6a); 3.68 (dd, 1H, H6b, $J_{H6b-H5}$=1.6 Hz, $J_{H6b-H6a}$=11.1 Hz); 2.04 (s, 3H, CH$_3$).

EXAMPLE 15

Synthesis of a Glycosyl Acceptor Synthon of General Formula (II) According to the Invention Step 15A Preparation of Benzyl 2-O-acetyl-3-O-allyl-4,6-di-O-benzyl-β-D-gluco-pyranoside Precursor.

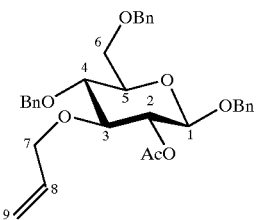

1.62 mL (3 eq.) of benzyl alcohol and 130 µL (0.1 eq.) of TESOTf are added to 3.07 g (1 eq.) of 2-O-acetyl-3-O-allyl-4,6-di-O-benzyl-α-D-gluco-pyranosyl trichloroacetimidate (M=586.5) in 25 mL of dichloromethane at 0° C. in the presence of 2.5 g of 4 Å molecular seives. After 1 hour of reaction at 0° C., the medium is neutralised with triethylamine, filtered and concentrated. Purification over silica gel [flash; eluent: toluene/ethyl acetate (98/2; v/v)] enables isolating 2.52 g of benzyl 2-O-acetyl-3-O-allyl-4,6-di-O-benzyl-β-D-glucopyranoside (M=532).

TLC: Rf=0.5 [toluene/ethyl acetate (9/1; v/v)]. Colourless oil. Yield (%)=91.

$^{13}$C NMR (CDCl$_3$, 100 MHz) δ (ppm): 169.55 (C=O); 138.20, 137.99, 137.47 (C quat. arom.); 134.75 (C8);

128.51, 128.46, 128.41, 128.13, 128.01, 127.94, 127.83, 127.74, 127.71, 127.67, 127.64 (C arom.); 117.04 (C9); 99.72 (C1); 82.73 (C3); 77.78 (C4); 75.22 (C5); 75.09 (CH$_2$—Ar); 73.94 (C7); 73.58 (CH$_2$—Ar); 73.08 (C2); 70.36 (CH$_2$—Ar sur C1); 68.81 (C6); 21.13 (CH3).

$^1$H NMR (CDCl$_3$, 400 MHz) δ (ppm): 7.36–7.20 (m, 15H, H arom.); 5.85 (ddt, 1H, H8, $J_{H8-H7a}=J_{H8-H7b}=5.7$ Hz, $J_{H8-H9a}=17.2$ Hz, $J_{H8-H9b}=10.4$ Hz); 5.22 (ddt, 1H, H9a, $J_{H9a-H7}=1.6$ Hz, $J_{H9a-H8}=17.2$ Hz, $J_{H9a-H9b}=1.7$ Hz); 5.13 (ddt, 1H, H9b, $J_{H9b-H7}=1.2$ Hz, $J_{H9b-H8}=10.4$ Hz, $J_{H9b-H9a}=1.5$ Hz); 5.02 (dd, 1H, H2, $J_{H2-H1}=8.0$ Hz, $J_{H2-H3}=9.4$ Hz); 4.89 (d, 1H, CH$_2$—Ar, $^2J=12.4$ Hz); 4.80 (d, 1H, CH$_2$—Ar, $^2J=10.7$ Hz); 4.62 (d, 1H, CH$_2$—Ar, $^2J=12.0$ Hz); 4.61 (d, 1H, CH$_2$—Ar sur C1, $^2J=11.3$ Hz); 4.56 (d, 1H, CH$_2$—Ar, $^2J=12.2$ Hz); 4.55 (d, 1H, CH$_2$—Ar, $^2J=10.7$ Hz); 4.40 (d, 1H, H1, $J_{H1-H2}=8.0$ Hz); 4.24 (ddt, 1H, H7a, $J_{H7a-H7b}=12.6$ Hz, $J_{H7a-H8}=5.6$ Hz, $J_{H7a-H9}=1.4$ Hz); 4.12 (ddt, 1H, H7b, $J_{H7b-H7a}=12.6$ Hz, $J_{H7b-H8}=5.9$ Hz, $J_{H7b-H9}=1.4$ Hz); 3.75 (dd, 1H, H6a, $J_{H6a-H5}=2.0$ Hz, $J_{H6a-H6b}=11.0$ Hz); 3.70 (dd, 1H, H6b, $J_{H6b-H5}=4.7$ Hz, $J_{H6b-H6a}=10.9$ Hz); 3.64 (t, 1H, H4, $J_{H4-H3}=J_{H4-H5}=9.4$ Hz); 3.51 (t, 1H, H3, $J_{H3-H2}=J_{H3-H4}=9.3$ Hz); 3.45 (ddd, 1H, H5, $J_{H5-H4}=9.6$ Hz, $J_{H5-H6a}=2.0$ Hz, $J_{H5-H6b}=4.6$ Hz); 2.06 (s, 3H, CH$_3$).

Step 15B
Preparation of Synthon Acceptor Benzyl 2-O-acetyl-4,6-di-O-benzyl-β-D-gluco-pyranoside of (OH in Position 3).

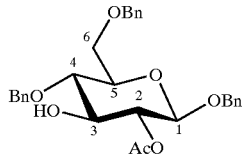

2.44 g (1 eq.) of benzyl 2-O-acetyl-3-allyl-4,6-di-O-benzyl-β-D-gluco-pyranoside of (M=532) are dissolved in 85 mL of an ethanol/toluene/water (8/3/1; v/v/v) mixture and then 3.86 g (7.5 eq.) of Dabco and 640 mg (0.15 eq.) of Wilkinson's catalyst are added thereto. The medium is refluxed for 2 hours and then concentrated. The mixture is taken up into dichloromethane, washed with iced water, with iced 5% HCl, iced 5% NaHCO$_3$, with iced water, dried (MgSO$_4$) and concentrated.

The residue is then dissolved in 48 mL of an acetone/10% aq. HCl (19/1; v/v) mixture and the solution is refluxed for 8 min, and then cooled to R.T., neutralised with 5% NaHCO$_3$ and concentrated. After taking up with dichloromethane and washings with water, purification over silica gel [flash; eluent: toluene/ethyl acetate (85/15; v/v)] leads to obtaining 1.32 g of benzyl 2-O-acetyl-4,6-di-O-benzyl-β-D-glucopyranoside (M=491).

TLC: Rf=0.3 [toluene/ethyl acetate (8/2; v/v)]. White solid. Yield (%)=59.

$^{13}$C NMR (CDCl$_3$, 100 MHz) δ (ppm): 170.96 (C=O); 138.12, 138.09, 137.37 (C quat. arom.); 128.63, 128.49, 128.44, 128.13, 128.07, 127.90, 127.82, 127.78, 127.69 (C arom.); 99.47 (C1); 78.34 (C3); 75.98 (C4); 74.98 (C5); 74.87 (CH$_2$—Ar);74.40 (C2); 73.64 (CH$_2$—Ar); 70.53 ( CH$_2$—Ar sur C1); 68.77 (C6); 21.03 (CH3).

$^1$H NMR (CDCl$_3$, 400 MHz) δ (ppm): 7.38–7.23 (m, 15H, H arom.); 4.91 (d, 1H, CH$_2$—Ar, $^{2\,J=12.4}$ Hz); 4.88 (dd, 1H, H2, $J_{H2-H1}=7.9$ Hz, $J_{H2-H3}=9.4$ Hz); 4.78 (d, 1H, CH$_2$—Ar, $^{2\,J=11.2}$ Hz); 4.66 (d, 1H, CH$_2$—Ar, $^{2\,J=12.2}$ Hz); 4.62 (d, 1H, CH$_2$—Ar, $^2J=12.2$ Hz); 4.62 (d, 1H, CH$_2$—Ar, $^2J=11.4$ Hz); 4.58 (d, 1H, CH$_2$—Ar, $^2J=12.1$ Hz); 4.46 (d, 1H, H1, $J_{H1-H2}=7.9$ Hz); 3.79 (dd, 1H, H6a, $J_{H6a-H5}=2.2$ Hz, $J_{H6a-H6b}=10.9$ Hz); 3.74 (dd, 1H, H6b, $J_{H6b-H5}=4.4$ Hz, $J_{H6b-H6a}=10.9$ Hz); 3.72 (t, 1H, H3, $J_{H3-H2}=J_{H3-H4}=9.1$ Hz); 3.60 (dd, 1H, H4, $J_{H4-H3}=8.8$ Hz, $J_{H4-H5}=9.6$ Hz); 3.45 (ddd, 1H, H5, $J_{H5-H4}=9.6$ Hz, $J_{H5-H6a}=2.2$ Hz, $J_{H5-H6b}=4.4$ Hz); 2.39 (d, 1H, OH, J=4.1 Hz), 2.09 (s, 3H, CH$_3$).

EXAMPLE 16

Synthesis of a Disaccharide According to the Invention

This Example illustrates the interest of the method according to the invention for the preparation of a disaccharide by a reaction of coupling between two monosaccharides, it being possible for the disaccharide obtained itself to act as a precursor of a disaccharide glycosyl acceptor (see Example 17) for the synthesis of a trisaccharide (see Example 18).

Synthesis of Benzyl 2-O-acetyl-3-O-allyl-4,6-di-O-benzyl-β-D-glucopyranosyl-(1→3)-2-O-acetyl-4,6-di-O-benzyl-β-D-glucopyranoside.

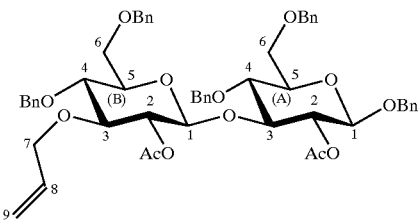

1.73 g (1.1 eq.) of 2-O-acetyl-3-O-allyl-4,6-di-O-benzyl-α-D-glucopyranosyl trichloroacetimidate prepared in Example 14 (M=586.5) and 1.32 g (1 eq.) of benzyl 2-O-acetyl-4,6-di-O-benzyl-β-D-glucopyranoside prepared in Example 15 (M=491) are introduced into 30 mL of anhydrous dichloromethane at 0° C. in the presence of 4 Å molecular sieves (3 g), and then 150 μL (0.25 eq.) of TESOTf. After 1 hour of reaction at 0° C., the medium is neutralised with triethylamine, filtered and concentrated. The product is purified over silica gel [flash; eluent: toluene/ethyl acetate (95/5; v/v)] and 1.87 g of benzyl 2-O-acetyl-3-O-allyl-4,6-di-O-benzyl-β-D-glucopyranosyl-(1→3)-2-O-acetyl-4,6-di-O-benzyl-β-D-glucopyranoside (M=915) are thus collected.

TLC: Rf=0.3 [toluene/ethyl acetate (9/1; v/v)]. Colourless oil. Yield (%)=76.

$^{13}$C NMR (CDCl$_3$, 100 MHz) δ (ppm): 170.04, 169.12 (C=O); 138.46, 138.28, 138.22, 137.84, 137.38 (C quat. arom.); 134.64 (C8B); 128.54, 128.45, 128.44, 128.40, 128.36, 128.22, 128.17, 128.00, 127.83, 127.77, 127.69, 127.63, 127.56 (C arom.); 117.10 (C9B); 100.86 (C1B); 99.22 (C1A); 82.95 (C3B); 80.44 (C3A); 77.93 (C4B); 75.88 (C4A); 75.50 (C5B); 75.15 (C5A); 75.10 (CH$_2$—Ar); 74.98 (CH$_2$—Ar); 73.99 (C7B); 73.63 (C2A); 73.53 ( CH$_2$—Ar); 73.48 (CH$_2$—Ar); 73.05 (C2B); 70.28 ( CH$_2$—Ar sur C1A); 69.14, 69.04 (C6A, C6B); 21.07, 20.96 (CH3).

$^1$H NMR (CDCl$_3$, 400 MHz) δ (ppm): 7.35–7.18 (m, 25H, H arom.); 5.85 (ddt, 1H, H8B, $J_{H8B-H7aB}=J_{H8B-H7bB}=5.7$ Hz, $J_{H8B-H9aB}=17.2$ Hz, $J_{H8B-H9bB}=10.4$ Hz); 5.23 (ddt, 1H, H9aB, $J_{H9aB-H7B}=1.6$ Hz, $J_{H9aB-H8B}=17.2$ Hz, $J_{H9aB-H9bB}=1.7$ Hz); 5.14 (ddt, 1H, H9bB, $J_{H9bB-H7B}=1.2$ Hz, $J_{H9bB-H8B}=10.4$ Hz, $J_{H9bB-H9aB}=1.5$ Hz); 5.03 (d, 1H, CH2—Ar, $^2J=11.01$ Hz); 5.00 (dd, 1H, H2A, $J_{H2A-H1A}=8.0$ Hz, $J_{H2A-H3A}=9.6$ Hz); 4.95 (dd, 1H, H2B, $J_{H2B-H1B}=8.2$ Hz, $J_{H2B-H3B}=9.6$ Hz); 4.88 (d, 1H, CH$_2$—Ar sur C1A, $^2J=12.4$ Hz); 4.78 (d, 1H, CH$_2$—Ar, $^2J=10.8$ Hz); 4.58 (d, 1H, CH$_2$—Ar, $^2J$=12.1 Hz); 4.57 (d, 1H, H1B, $J_{H1B-H2B}$=8.0 Hz); 4.57 (d, 1H, CH$_2$—Ar sur C1A, $^2J$=13.4 Hz); 4.54 (d, 1H, CH$_2$—Ar, $^2J$=12.2 Hz); 4.52 (d, 1H, CH$_2$—Ar, $^2J$=10.7 Hz); 4.47 (d, 1H, CH$_2$—Ar, $^2J$=10.9 Hz); 4.41 (d, 1H, CH$_2$—Ar, $^2J$=12.1 Hz); 4.36 (d, 1H, CH$_2$—Ar, $^2J$=14.0 Hz); 4.33 (d, 1H, H1A, $J_{H1A-H2A}$=8.0 Hz); 4.25 (ddt, 1H, H7aB, $J_{H7aB-H7bB}$=12.6 Hz, $J_{H7aB-H8B}$=5.6 Hz, $J_{H7aB-H9B}$=1.4 Hz); 4.11 (ddt, 1H, H7bB, $J_{H7bB-H7aB}$=12.6 Hz, $J_{H7bB-H8B}$=5.9 Hz, $J_{H7bB-H9B}$=1.4 Hz); 3.94 (dd, 1H, H3A, $J_{H3A-H2A}$=9.3 Hz, $J_{H3A-H4A}$=8.8 Hz); 3.74 (dd, 1H, H6aA or H6aB, $J_{H6a-H5}$=2.0 Hz, $J_{H6a-H6b}$=10.8 Hz); 3.73 (dd, 1H, H6aA or H6aB, $J_{H6a-H5}$=1.6 Hz, $J_{H6a-H6b}$=10.7 Hz); 3.64 (dd, 1H, H6bA or H6bB, $J_{H6b-H5}$=5.1 Hz, $J_{H6b-H6a}$=10.8 Hz); 3.61 (t, 1H, H$_4$B, $J_{H4B-H3B}$=$J_{H4B-H5B}$=9.2 Hz); 3.56 (dd, 1H, H4A, $J_{H4A-H3A}$=8.9 Hz, $J_{H4A-H5A}$=9.4 Hz); 3.53 (dd, 1H, H6bA or H6bB, $J_{H6b-H5}$=5.2 Hz, $J_{H6b-H6a}$=10.9 Hz); 3.47 (t, 1H, H3B, $J_{H3B-H2B}$=$J_{H3B-H4B}$=9.2 Hz); 3.47–3.41 (m, 2H, H5A, H5B), 2.10 (s, 3H, CH$_3$); 2.05 (s, 3H, CH$_3$).

EXAMPLE 17

Synthesis of a Disaccharide Glycosyl Acceptor According to the Invention

Synthesis of Benzyl 2-O-acetyl-4,6-di-O-benzyl-β-D-glucopyranosyl-(1→3)-2-O-acetyl-4,6-di-O-benzyl-β-D-glucopyranoside.

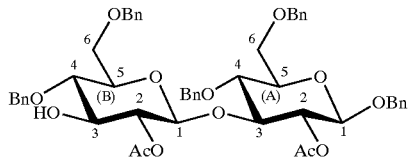

1.28 g (1 eq.) of benzyl 2-O-acetyl-3-O-allyl-4,6-di-O-benzyl-β-D-gluco-pyranosyl-(1→3)-2-O-acetyl-4,6-di-O-benzyl-β-D-glucopyranoside (M=915) and 1.18 g of Dabco are dissolved in 50 ml of an ethanol/toluene/water (8/3/1; v/v/v) mixture and then 390 mg (0.3 eq.) of Wilkinson's catalyst are added thereto. The reaction medium is heated under reflux for 1 hour 30 minutes and then put to dryness. The mixture is then taken up with dichloromethane and extracted with water, with iced 1/2N HCl, with 5% NaHCO$_3$ and then with water, dried and concentrated. The residue is then redissolved in 30 ml of an acetone/10% aq. HCl (19/1; v/v) mixture which is refluxed for 8 min. After rapid cooling to R.T., the solution is neutralised with a few drops of 5% NaHCO$_3$ and concentrated. The whole is diluted again with dichloromethane and is extracted with water. The product is finally purified over silica gel [flash; eluent: toluene/ethyl acetate (85/15; v/v)] which thus enables isolating 600 mg of benzyl 2-O-acetyl-4,6-di-O-benzyl-β-D-glucopyranosyl-(1→3)-2-O-acetyl-4,6-di-O-benzyl-β-D-glucopyranoside (M=875).

TLC: Rf=0.3 [toluene/ethyl acetate (8/2; v/v)]. Colourless oil. Yield (%)=49.

$^{13}$C NMR (CDCl$_3$, 100 MHz) δ (ppm): 171.65, 169.09 (C=O); 138.49, 138.24, 137.99, 137.37 (C quat. arom.); 128.61, 128.43, 128.39, 128.29, 128.23, 128.14, 128.07, 127.78, 127.76, 127.66, 127.61, 127.59, 127.57 (C arom.); 100.64 (C1B); 99.22 (C1A); 80.70 (C3A); 78.50 (C4B); 76.39 (C3B); 75.96 (C4A); 75.31, 75.17 (C5A, C5B); 74.97, 74.89 (CH$_2$—Ar); 74.31 (C2B); 73.53, 73.51, (C2A, 2 CH$_2$—Ar); 70.25 (CH$_2$—Ar sur C1A); 69.16, 69.01 (C6A, C6B); 21.07, 20.85 (CH3).

$^1$H NMR (CDCl$_3$, 400 MHz) δ (ppm): 7.34–7.19 (m, 25H, H arom.); 5.04 (d, 1H, CH$_2$—Ar, $^2J$=10.1 Hz); 5.03 (dd, 1H, H2A, $J_{H2A-H1A}$=8.1 Hz, $J_{H2A-H3A}$=9.8 Hz); 4.88 (d, 1H, CH$_2$—Ar sur C1A, $^2J$=12.4 Hz); 4.80 (dd, 1H, H2B, $J_{H2B-H1B}$=8.1 Hz, $J_{H2B-H3B}$=9.4 Hz); 4.76 (d, 1H, CH$_2$—Ar, $^2J$=11.1 Hz); 4.62 (d, 1H, H1B, $J_{H1B-H2B}$=8.5 Hz); 4.60 (d, 1H, CH$_2$—Ar, $^2J$=11.5 Hz); 4.58 (d, 1H, CH$_2$—Ar, $^2J$=12.2 Hz); 4.57 (d, 1H, CH$_7$Ar sur C1A, $^2J$=12.3 Hz); 4.53 (d, 1H, CH$_2$—Ar, $^2J$=12.2 Hz); 4.47 (d, 1H, CH$_2$—Ar, $^2J$=11.0 Hz); 4.40 (s, 2H, CH$_2$—Ar); 4.34 (d, 1H, H1A, $J_{H1A-H2A}$=8.0 Hz); 3.95 (t, 1H, H3A, $J_{H3A-H2A}$=$J_{H3A-H4A}$=9.1 Hz); 3.76 (dd, 1H, H6aA or H6aB, $J_{H6a-H5}$=1.6 Hz, $J_{H6a-H6b}$=11.6 Hz); 3.74 (dd, 1H, H6aA or H6aB, $J_{H6a-H5}$=1.7 Hz, $J_{H6a-H6b}$=11.8 Hz); 3.69 (m, 1H, H3B); 3.65 (dd, 1H, H6bA or H6bB, $J_{H6b-H5}$=5.0 Hz, $J_{H6b-H6a}$=10.8 Hz); 3.57 (t, 1H, H4A, $J_{H4A-H3A}$=$J_{H4A-H5A}$=9.3 Hz); 3.57 (dd, 1H, H6bA or H6bB, $J_{H6b-H5}$=5.4 Hz, $J_{H6b-H6a}$=11.3 Hz); 3.55 (t, 1H, H4B, $J_{H4B-H3B}$=$J_{H4B-H5B}$=8.6 Hz); 3.43 (m, 2H, H5A, H5B); 2.49 (d, 1H, OH, J=4.1 Hz); 2.13 (s, 3H, CH$_3$); 2.04 (s, 3H, CH$_3$).

EXAMPLE 18

Synthesis of a Trisaccharide According to the Invention

This Example illustrates the interest of the method according to the invention for the preparation of a trisaccharide by a reaction of coupling between a monosaccharide and a disaccharide, it being possible for the trisaccharide obtained itself to act as a glycosyl acceptor precursor for the synthesis of a tetrasaccharide, and so forth.

Synthesis of Benzyl 2-O-acetyl-3-O-allyl-4,6-di-O-benzyl-β-D-glucopyranosyl-(1→3)-2-O-acetyl-4,6-di-O-benzyl-β-D-glucopyranosyl-(1→3)-2-O-acetyl-4,6-di-O-benzyl-β-D-glucopyranoside.

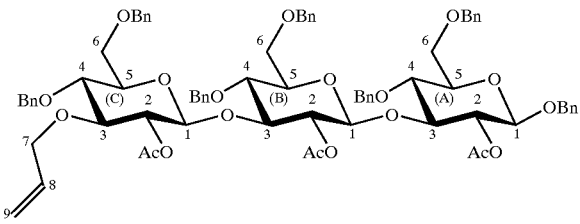

600 mg (1.1 eq.) of 2-O-acetyl-3-O-allyl-4,6-di-O-benzyl-α-D-glucopyranosyl trichloroacetimidate prepared in Example 14 (M=586.5) and 540 mg (1 eq.) of benzyl 2-O-acetyl-4,6-di-O-benzyl-β-D-glucopyranosyl-(1→3)-2-O-acetyl-4,6-di-O-benzyl-β-D-glucopyranoside prepared in Example 17 (M=875) are introduced into 10 mL of anhydrous dichloromethane in the presence of 1 g of 4 Å molecular sieves at 0° C. 35 μL (0.25 eq.) of TESOTf are then added thereto. After 50 min of reaction at 0° C., the medium is neutralised with triethylamine, filtered and concentrated. Purification over silica gel [flash; eluent: toluene/ethyl acetate (9/1; v/v)] leads to obtaining 500 mg of benzyl 2-O-acetyl-3-O-allyl-4,6-di-O-benzyl-β-D-glucopyranosyl-(1→)-2-O-acetyl-4,6-di-O-benzyl-β-D-glucopyranosyl-(1→)-2-O-acetyl-4,6-di-O-benzyl-β-D-glucopyranoside (M=1299).

TLC: Rf=0.4 [toluene/ethyl acetate (9/1; v/v)]. Colourless oil. Yield (%)=63.

$^{13}$C NMR (CDCl$_3$, 100 MHz) δ (ppm): 170.09, 169.44, 169.29 (C=O); 138.46, 138.43, 138.35, 138.20, 138.17, 137.85, 137.36 (C quat. arom.); 134.58 (C8C); 128.47–127.37 (C arom.); 117.13 (C9C); 101.13 (C1C); 100.43 (C1B); 99.21 (C1A); 82.92 (C3C); 80.96 (C3B); 80.23 (C3A); 77.88 (C4C); 76.13 (C4B); 75.89 (C4A);

75.45, 75.08, 75.02, 74.99, 74.96 (2 $\underline{C}H_2$—Ar, C5A, C5B, C5C); 74.03 (C7C); 73.69, 73.52, 73.51, 73.46, 73.42, 72.95 (3 $\underline{C}H_2$—Ar, C2A, C2B, C2C); 70.30 ($\underline{C}H_2$—Ar sur C1A); 69.40, 69.18, 69.00 (C6A, C6B, C6C); 21.19, 21.02, 20.99 (CH3).

$^1$H NMR (CDCl$_3$, 400 MHz) δ (ppm): 7.34–7.19 (m, 35H, H arom.); 5.85 (ddt, 1H, H8C, $J_{H8C-H7aC}=J_{H8C-H7bC}=5.7$ Hz, $J_{H8C-H9aC}=17.2$ Hz, $J_{H8C-H9bC}=10.4$ Hz); 5.23 (ddt, 1H, H9aC, $J_{H9aC-H7C}=1.6$ Hz, $J_{H9aC-H8C}=17.2$ Hz, $J_{H9aC-H9bC}=1.7$ Hz); 5.15 (ddt, 1H, H9bC, $J_{H9bC-H7C}=1.2$ Hz, $J_{H9bC-H8C}=10.4$ Hz, $J_{H9bC-H9ac}=1.5$ Hz); 5.03 (d, 1H, CH$_2$—Ar, $^2J=10.7$ Hz); 5.01 (d, 1H, CH$_2$—Ar, $^2J=10.1$ Hz); 4.97 (dd, 1H, H2A, $J_{H2A-H1A}=8.0$ Hz, $J_{H2A-H3A}=9.2$ Hz); 4.96 (dd, 1H, H2C, $J_{H2c-H}1C=8.1$ Hz, $J_{H2c-H3c}=9.4$ Hz); 4.92 (dd, 1H, H2B, $J_{H2B-H1B}=8.2$ Hz, $J_{H2B-H3B}=9.5$ Hz); 4.87 (d, 1H, CH$_2$—Ar sur C1A, $^2J=12.4$ Hz); 4.78 (d, 1H, CH$_2$—Ar, $^2J=10.6$ Hz); 4.58–4.28 (m, 3H, CH$_2$—Ar); 4.56 (d, 1H, H1C, $J_{H1C-H2c}=8.1$ Hz); 4.56 (d, 1H, CH2—Ar sur C1A, $^2J=12.1$ Hz); 4.52 (d, 1H, CH2—Ar, $^{2J}=10.8$ Hz); 4.49 (d, 1H, H1B, $J_{H1B-H2B}=8.0$ Hz); 4.47 (d, 1H, CH$_2$—Ar, $^2J=10.8$ Hz); 4.46 (d, 1H, CH2—Ar, $^2J=11.2$ Hz); 4.37 (d, 1H, CH2—Ar, $^2J=12.3$ Hz); 4.33 (d, 1H, CH2—Ar, $^2J=11.9$ Hz); 4.32 (d, 1H, H1A, $J_{H1A-H2A}=7.9$ Hz); 4.30 (d, 1H, CH2—Ar, $^2J=12.3$ Hz); 4.24 (m, 1H, H7aC); 4.12 (ddt, 1H, H7bC, $J_{H7bC-H7aC}=12.6$ Hz, $J_{H7bC-H8C}=5.9$ Hz, $J_{H7bC-H9C}=1.4$ Hz); 3.92 (t, 1H, H3A, $J_{H3A-H2A}=J_{H3A-H4A}=9.0$ Hz); 3.89 (dd, 1H, H3B, $J_{H3B-H2B}=9.4$ Hz, $J_{H3B-H4B}=8.6$ Hz); 3.75–3.40 (m, 3H, H5A, H5B, H5C); 3.74–3.70 (m, 2H, H6); 3.64–3.59 (m, 2H, H6); 3.62 (t, 1H, H4C, $J_{H4C-H3C}=J_{H4C-H5C}=9.3$ Hz); 3.53–3.40 (m, 2H, H6); 3.53 (t, 1H, H4A, $J_{H4A-H3A}=J_{H4A-H5A}=9.1$ Hz); 3.51 (dd, 1H, H4B, $J_{H4B-H3B}=8.7$ Hz, $J_{H4B-H5B}=9.4$ Hz); 3.48 (t, 1H, H3C, $J_{H3C-H2C}=J_{H3C-H4C}=9.1$ Hz); 2.12 (s, 3H, CH$_3$); 2.10 (s, 3H, CH$_3$); 2.02 (s, 3H, CH$_3$).

What is claimed is:

1. A method of preparing functionalized β-(1,3)-glucans comprising a reaction between a glycosyl donor and a glycosyl acceptor, wherein the glycosyl donor is selected from the group consisting of the compounds of formulae Ia and Ib:

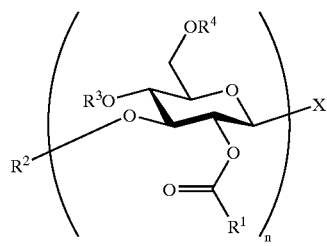

Ia

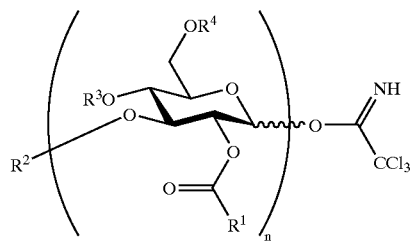

Ib in which:

X is a leaving group selected from the group consisting of:
  a group of formula $S(O)_p R_a$, in which $R_a$ is selected from the group consisting of an alkyl radical having 1 to 18 carbon atoms, 1,1-dicyclohexymethyl, an aryl radical which is non-substituted or substituted by an alkyl or alkoxy group having 1 to 6 carbon atoms, a nitro and an acetamide group, and p is an integer equal to 0 or 1;

$R^1$ is selected from the group consisting of:
  an alkyl, haloalkyl or ketoalkyl radical having 1 to 6 carbon atoms;
  an aryl radical which is non-substituted or substituted with one or more groups selected from the group consisting of a halogen atom, an alkoxy radical having 1 to 6 carbon atoms and a nitro group;

$R^3$ and $R^4$, which are different from —CO—$R^1$ and from $R^2$, independently represent a benzyl, chlorobenzyl, methoxybenzyl, nitrobenzyl, allyl, methylnaphthyl, chloroacetyl, trialkylsilyl or triarylmethyl radical;

or together form an ethylidyl, isopropylidyl, hexafluoroisopropylidyl, cyclopentylidyl, cyclohexylidyl, cycloheptylidyl, butylidyl, 1-tert-butylethylidyl, benzylidyl, methoxybenzylidyl or 1-phenylbenzylidyl radical;

$R^2$ is a methylnaphthyl radical;

n is an integer of between 1 and 4; it being specified that in the case in which n is greater than 1, it is possible for —COR$^1$, R$^3$ and R$^4$ to be different from one glycosyl unit to another;

and wherein the glycosyl acceptor selected from the group consisting of the compounds of formula II:

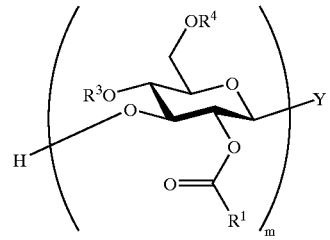

II in which:

Y is:
  a group of formula —O—R$_b$ in which R$_b$ is an alkyl radical having 1 to 24 carbon atoms, an alkenyl radical having 2 to 24 carbon atoms or an arylalkylaryl or arylalkyl radical having 6 to 18 carbon atoms;
  a serine or threonine;
  a sterol;
  a glycerolipid;
  a group of formula —S—R$_a$ in which R$_a$ is as defined above;

$R^1$, $R^3$ and $R^4$ are as defined above and;

m is an integer of between 1 and 8, it being specified that in the case in which m is greater than 1, it is possible for —COR$^1$, R$^3$ and R$^1$ to be different from one glycosyl unit to another, wherein said reaction is carried out in solution in an anhydrous organic solvent, at a temperature between –80° C. and 40° C., for a period of 1 minute to 8 hours, in the presence of a promoter.

2. The method according to claim 1, wherein the glycosyl donor cited above is a compound of formulae (Ia) or (Ib) in which:

X is a leaving group selected from the group consisting of:
a group of formula $S(O)_pR_a$, in which $R_a$ is an alkyl radical having 1 to 5 carbon atoms, a non-substituted aryl radical or an aryl radical which is substituted with an alkyl group having 1 to 6 carbon atoms, and p is an integer equal to 0 or 1;

$R^1$ is:
an alkyl radical having 1 to 6 carbon atoms;
a non-substituted aryl radical;

$R^3$ and $R^4$, which are different from —CO—$R^1$ and from $R^2$, independently represent a benzyl, chlorobenzyl, methoxybenzyl, nitrobenzyl, allyl, methylnaphthyl, chloroacetyl, trialkylsilyl or triarylmethyl radical;
or together form an ethylidyl, isopropylidyl or benzylidyl radical;

n is an integer equal to 1, 2 or 3; it being specified that in the case in which n is equal to 2 or 3, it is possible for —COR$^1$, R$^3$ and R$^4$ to be different from one glycosyl unit and another.

3. The method according to claim 2, wherein the glycosyl donor cited above is a compound of formulae (Ia) or (Ib) in which:

X represents a leaving group selected from the group consisting of:
a group of formula $SR_a$, in which $R_a$ is an ethyl, propyl, butyl, phenyl or toluyl radical;

$R^1$ is methyl or phenyl;

$R^3$ and $R^4$, which are different from —CO—$R^1$ and from $R^2$, independently represent a benzyl or methoxybenzyl radical
or together form a benzylidyl radical;

n is an integer equal to 1 or 2; it being specified that in the case in which n is equal to 2, it is possible for —COR$^1$, $R^3$ and $R^4$ to be different from one glycosyl unit and another.

4. The method according to claim 3, wherein the glycosyl donor cited above is a compound of formulae (Ia) or (Ib) in which:

X represents a leaving group selected from the group consisting of:
a group of formula $SR_a$, in which $R_a$ is an ethyl or phenyl;

$R^1$ is a methyl or phenyl;

$R^3$ and $R^4$, which are different from —CO—$R^1$ and from $R^2$, independently represent a benzyl or methoxybenzyl radical,
or together form a benzylidyl radical;

n is an integer equal to 1.

5. The method according to claim 2 wherein the glycosyl acceptor is a compound of formula (II) in which:

Y represents a group selected from the group consisting of:
a group of formula —O—$R_b$ in which $R_b$ is an alkyl radical having 1 to 24 carbon atoms, an alkenyl radical having 2 to 24 carbon atoms or an arylalkylaryl or arylalkyl radical having 6 to 18 carbon atoms;
a serine or threonine;
a sterol;
a glycerolipid;
a group of formula —S—$R_a$ in which $R_a$ is as defined in claim 2;

$R^1$, $R^3$ and $R^4$ are as defined in claim 2, and;

m in an integer of between 1 and 8, it being specified that in the case in which m is greater than 1, it is possible for —COR$^1$, $R^3$ and $R^4$ to be different from one glycosyl unit and another.

6. The method according to claim 5 wherein the glycosyl acceptor is a compound of formula (II) in which:

Y is:
a group of formula —O—$R_b$ in which $R_b$ is an alkyl radical having 1 to 24 carbon atoms, an alkenyl radical having 2 to 24 carbon atoms or a benzyl radical;

$R^1$, $R^3$ and $R^4$ are as defined in claim 5;

m in an integer of between 1 and 8, it being specified that in the case in which m is greater than 1, it is possible for —COR$^1$, $R^3$ and $R^4$ to be different from one glycosyl unit and another.

7. The method according to claim 6, wherein the glycosyl acceptor is a compound of formula (II) in which:

$R^1$ is a methyl or phenyl radical;

$R^3$ and $R^4$, which are different from —CO—$R^1$ independently represent a benzyl or methoxybenzyl radical
or together form a benzylidyl radical.

8. The method of preparing functionalized β-(1,3)-glucans according to claim 1, wherein the promoter is selected from the group consisting of;

N-bromosuccinimide or N-iodosuccinimide, combined with a Lewis acid selected from the group consisting of ferric chloride, copper ditriflate, tin ditriflate, bores trifluoride dietherate, tin or zirconium tetrachloride, methyl inflate, trimethyl- (or triethyl-) silyl triflate, silver triflate, cadmium ditriflate, cobalt ditriflate, nickel ditriflate, zinc ditriflate, bismuth tritriflate, iron tritriflate, and gallium tritriflate, in the case of glycosyl donors of formula Ia in which X represents an $S(O)_pR_a$ group in which p is equal to 0, a Lewis acid selected from the group consisting of triflic anhydride, ferric chloride, copper ditriflate, tin ditriflate, boron trifluoride dietherate, tin or zirconium tetrachloride, methyl triflate, trimethyl- (or triethyl-) silyl triflate, silver triflate, cadmium ditriflate, cobalt ditriflate, nickel ditriflate, zinc ditriflate, bismuth tritriflate, iron triflate, and gallium tritriflate, combined with an amine, in the case of glycosyl donors of formula Ia in which X represents an $S(O)_pR_a$ group in which p is equal to 1, and a Bronsted acid or a Lewis acid selected from the group consisting of triflic anhydride, ferric chloride, copper ditriflate, tin ditriflate, boron trifluoride dietherate, tin or zirconium tetrachloride, methyl triflate, trimethyl- (or triethyl-) silyl triflate, silver triflate, cadmium ditriflate, cobalt ditriflate, nickel ditriflate, zinc ditriflate, bismuth tritriflate, iron tritriflate, and gallium tritriflate, in the case of glycosyl donors of formula Ib.

9. The method of preparing functionalized β-(1,3)-glucans according to claim 1, wherein the reaction between the glycosyl donor and a glycosyl acceptor is followed by deprotection treatment.

10. A glycosyl acceptor synthon for implementing the method according to claim 1 which is a compound of formula II:

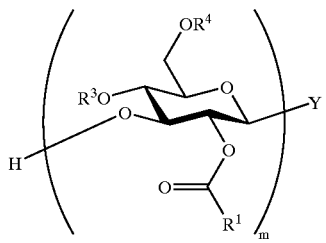

in which:
Y is a group selected from the group consisting of:
  a group of formula —O—$R_b$ in which $R_b$ is an arylalkylaryl or arylalkyl radical having 6 to 18 carbon atoms;
  a serine or threonine;
  a sterol;
  a glycerolipid;
$R^1$ is:
  an alkyl, haloalkyl or ketoalkyl radical having 1 to 6 carbon atoms;
  an aryl radical which is non-substituted or substituted with one or more groups selected from a halogen atom, an alkoxy radical having 1 to 6 carbon atoms or a nitro group;
$R^3$ and $R^4$, which are different from —CO—$R^1$ and from $R^2$, independently are a benzyl, chlorobenzyl, methoxybenzyl, nitrobenzyl, allyl, methylnaphthyl, chloroacetyl, trialkylsilyl or triarylmethyl radical;
or together form an ethylidyl, isopropylidyl, hexafluoroisopropylidyl, cyclopentylidyl, cyclohexylidyl, cycloheptylidyl, butylidyl, 1-tert-butylethylidyl, benzylidyl, methoxybenzylidyl or 1-phenylbenzylidyl radical;
m is an integer of between 1 and 8, it being specified that in the case in which m is greater than 1, it is possible for —COR$^1$, $R^3$ and $R^4$ to be different from one glycosyl unit and another.

11. The glycosyl acceptor synthon according to claim 10, which is a compound of formula (II) in which:
Y is a group selected from the group consisting of:
  a group of formula —O—$R_b$ in which $R_b$ is an arylalkylaryl or arylalkyl radical having 6 to 18 carbon atom.;
  a serine or threonine;
  a sterol;
  a glycerolipid;
$R^1$ is:
  an alkyl, haloalkyl or ketoalkyl radical having 1 to 6 carbon atoms;
  an aryl radical which is non-substituted or substituted with one or more groups selected from a halogen atom, an alkoxy radical having 1 to 6 carbon atoms or a nitro group;
$R^3$ and $R^4$, which are different from —CO—$R^1$ and from $R^2$, independently are a benzyl, chlorobenzyl, methoxybenzyl, nitrobenzyl, allyl, methylnaphthyl, chloroacetyl, trialkylsilyl or triarylmethyl radical;
or together form an ethylidyl, isopropylidyl, hexafluoroisopropylidyl, cyclopentylidyl, cyclohexylidyl, cycloheptylidyl, butylidyl, 1-tert-butylethylidyl, benzylidyl, methoxybenzylidyl or 1-phenylbenzylidyl radical;
m is an integer of between 1 and 8, it being specified that in the case in which m is greater than 1, it is possible for —COR$^1$, $R^3$ and $R^4$ to be different from one glycosyl unit to another.

12. The glycosyl acceptor synthon according to claim 11, which is a compound of formula (II) in which;
Y is a group selected from the group consisting of:
  a group of formula —O—$R_b$ in which $R_b$ is a benzyl radical;
$R^1$ is:
  an alkyl, haloalkyl or ketoalkyl radical having 1 to 6 carbon atoms;
  an aryl radical which is non-substituted or substituted with one or more groups selected from a halogen atom, an alkoxy radical having 1 to 6 carbon atoms or a nitro group;
$R^3$ and $R^4$, which are different from —CO—$R^1$ and from $R^2$, independently are a benzyl, chlorobenzyl, methoxybenzyl, nitrobenzyl, allyl, methylnaphthyl, chloroacetyl, trialkylsilyl or triarylmethyl radical;
or together form an ethylidyl, isopropylidyl, hexafluoroisopropylidyl, cyclopentylidyl, cyclohexylidyl, cycloheptylidyl, butylidyl, 1-tort-butylethylidyl, benzylidyl, methoxybenzylidyl or 1-phenylbenzylidyl radical;
m is an integer of between 1 and 8, it being specified that in the case in which m is greater than 1, It is possible for —COR$^1$, $R^3$ and $R^4$ to be different from one glycosyl unit to another.

13. The glycosyl acceptor synthon according to claim 12, which is a compound of formula (II) in which;
Y is an —O-benzyl group;
$R^1$ is a methyl or phenyl radical;
$R^3$ and $R^4$, independently are a benzyl or methoxybenzyl radical or together form a benzylidyl radical.

14. A glycosyl donor synthon for implementing the method according to claim 1 which is selected from the group consisting of the compounds of formulae Ia and Ib:

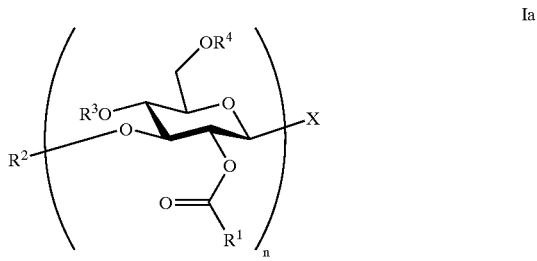

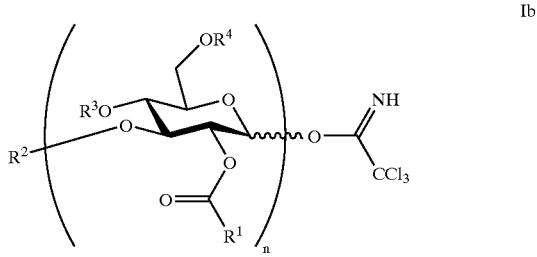

in which
X is a leaving group selected from the group consisting of:
  a group of formula $S(O)_p R_a$, in which $R_a$ is an alkyl radical having 1 to 18 carbon atoms, a 1,1-dicyclohexylmethyl radical, an aryl radical which is non-substituted or substituted with an alkyl or alkoxy group having 1 to 6 carbon atoms, a nitro or acetamide group, and p is an integer equal to 0 or 1;

$R^1$ is:
an alkyl, haloalkyl or ketoalkyl radical having 1 to 6 carbon atoms;
an aryl radical which is non-substituted or substituted with one or more groups selected from to group consisting of a halogen atom, an alkoxy radical having 1 to 6 carbon atoms and a nitro group;

$R^3$ and $R^4$, which are different from —CO—$R^1$ and from $R^2$, independently are a benzyl, chlorobenzyl, methoxybenzyl, nitrobenzyl, allyl, methylnaphthyl, chloroacetyl, trialkylsilyl or triarylmethyl radical;

or together form an ethylidyl, isopropylidyl, hexafluoroisopropylidyl, cyclopentylidyl, cyclohexylidyl, cycloheptylidyl, butylidyl, 1-tert-butylethylidyl, benzylidyl, methoxybenzylidyl or 1-phenylbenzylidyl radical;

$R^2$ is a methylnaphthyl radical; and n is an integer of between 1 and 4; it being specified that in the case in which n is greater than 1, it is possible for —COR$^1$, $R^3$ and $R^4$ to be different from one glycosyl unit to another; with the exception of 2-O-acetyl-3-O-allyl-4,6-benzylidene-α-D-glucopyranosyl trichloroacetimidate.

15. The glycosyl donor synthon according to claim 14 which is a compound of formulae (Ia) or (Ib) in which:

X is a leaving group selected from the group consisting of:
a group of formula $S(O)_pR_a$, in which $R_a$ is an alkyl radical having 1 to 5 carbon atoms, a non-substituted aryl radical and an aryl radical which is substituted with an alkyl group having 1 to 6 carbon atoms and p is an integer equal to 0 or 1;

$R^1$ is:
an alkyl radical having 1 to 6 carbon atoms, or a levulinyl group;
a non-substituted aryl radical;

$R^3$ and $R^4$, which are different from —CO—$R^1$ and from $R^2$, independently are a benzyl, chlorobenzyl, methoxybenzyl, nitrobenzyl, allyl, methylnaphthyl, chloroacetyl, trialkylsilyl or triarylmethyl radical;

or together form an ethylidyl, isopropylidyl or benzylidyl radical;

n is an integer equal to 1, 2 or 3; it being specified that in the case in which n is equal to 2 or 3, it is possible for —COR$^1$, $R^3$ and $R^4$ to be different from one glycosyl unit and another.

16. The glycosyl donor synthon according to claim 15 which is a compound of formulae (Ia) or (Ib) in which:

X is a leaving group selected from the group consisting of:
a group of formula $SR_a$, in which $R_a$ is ethyl, propyl, butyl or phenyl radical;

$R^1$ is a methyl or phenyl or toluyl radical;

$R^3$ and $R^4$, which are different from —CO—$R^1$ and from $R^2$, independently are a benzyl or methoxybenzyl radical or together form a benzylidyl radical;

n is an integer equal to 1 or 2; it being specified that in the case in which n is equal to 2, it is possible for —COR$^1$, $R^3$ and $R^4$ to be different from one glycosyl unit and another.

17. The glycosyl donor synthon according to claim 16 which is a compound of formulae (Ia) or (Ib) in which:

X is a leaving group selected from the group consisting of:
a group of formula $SR_a$, in which $R_a$ is an ethyl or phenyl radical;

$R^1$ is a methyl or phenyl radical;

$R^3$ and $R^4$ independently are a benzyl or methoxybenzyl radical,
or together form a benzylidyl radical;

n is an integer equal to 1.

* * * * *